(12) United States Patent
Nguyen et al.

(10) Patent No.: US 7,981,930 B2
(45) Date of Patent: *Jul. 19, 2011

(54) COMPOSITIONS AND KITS FOR TREATING INFLUENZA

(75) Inventors: Jack Nguyen, San Francisco, CA (US); Gregory T. Went, Mill Valley, CA (US); Paul Spence, Mill, CA (US); Timothy J. Fultz, Pleasant Hill, CA (US); David Chernoff, San Rafael, CA (US); Terry L. Burkoth, Palo Alto, CA (US); Rowan Chapman, Burlingame, CA (US); Mickey S. Urdea, Alamo, CA (US)

(73) Assignee: Adamas Pharmaceuticals, Inc., Emeryville, CA (US)

( * ) Notice: Subject to any disclaimer, the term of this patent is extended or adjusted under 35 U.S.C. 154(b) by 523 days.

This patent is subject to a terminal disclaimer.

(21) Appl. No.: 12/040,856

(22) Filed: Feb. 29, 2008

(65) Prior Publication Data

US 2008/0227743 A1   Sep. 18, 2008

Related U.S. Application Data

(60) Provisional application No. 60/918,011, filed on Mar. 13, 2007, provisional application No. 60/978,099, filed on Oct. 5, 2007, provisional application No. 60/989,790, filed on Nov. 21, 2007.

(51) Int. Cl.
*A61K 31/7056* (2006.01)
*A61K 31/351* (2006.01)
*A61K 31/215* (2006.01)
*A61K 31/196* (2006.01)
*A61K 31/195* (2006.01)
*A61K 31/131* (2006.01)
*C07H 19/056* (2006.01)
*C07D 309/28* (2006.01)
*C07C 69/75* (2006.01)
*C07C 61/22* (2006.01)
*C07C 229/48* (2006.01)
*C07C 211/38* (2006.01)

(52) U.S. Cl. .......... 514/529; 514/629; 514/43; 514/659; 514/661; 514/662; 514/459; 514/563; 536/28.7; 549/424; 560/128; 562/507; 564/456; 564/458; 564/459

(58) Field of Classification Search ............ None
See application file for complete search history.

(56) References Cited

U.S. PATENT DOCUMENTS

| 5,360,817 | A | 11/1994 | von Izstein et al. | |
|---|---|---|---|---|
| 5,866,601 | A | 2/1999 | Lew et al. | |
| 5,916,594 | A * | 6/1999 | Liebowitz et al. | 424/465 |
| 6,605,302 | B2 | 8/2003 | Faour et al. | |
| 7,619,007 | B2 * | 11/2009 | Went et al. | 514/662 |
| 2006/0008459 | A1 | 1/2006 | Johnson | |
| 2006/0035859 | A1 | 2/2006 | Carter et al. | |
| 2006/0247161 | A1 | 11/2006 | Planz et al. | |
| 2007/0270443 | A1 | 11/2007 | Went et al. | |
| 2008/0161324 | A1 | 7/2008 | Johansen et al. | |
| 2009/0247481 | A1 * | 10/2009 | Nguyen et al. | 514/43 |

FOREIGN PATENT DOCUMENTS

| WO | 01/45727 | 6/2001 |
|---|---|---|
| WO | WO 01/45727 A3 | 6/2002 |
| WO | 2007/057436 | 5/2007 |
| WO | WO 2007/057436 A3 | 7/2007 |

OTHER PUBLICATIONS

Merriam-Webster's Collegiate Dictionary, Tenth Edition, published 1998 by Merriam-Webster, incorporated, pp. 924 and 935.*
Drug labelling information for Symmatrel® (Amantadine Hydrochloride), approved Jul. 2002, pp. 1-12, downloaded from www.fda.gov.*
Deltenre, et al. Evaluation of amantadine in chronic hepatitis C: a meta-analysis. J Hepatol. Sep. 2004;41(3):462-73.
European search report and opinion dated Mar. 31, 2010 for Application No. 8732015.6.
Ilyushina, et al. Oseltamivir-ribavirin combination therapy for highly pathogenic H5N1 influenza virus infection in mice. Antimicrob Agents Chemother. Nov. 2008;52(11):3889-97.
International search report dated Jun. 3, 2008 for PCT Application No. US2008/56678.
Jean, et al. Proteomic profiling of host cellular proteins incorporated by severe acute respiratory syndrome (SARS)—associated coronavirus virions: Insights into emerging virus biology and new therapeutics targets. Abstracts of the 19th International Conference on Antiviral Research (ICAR). Antiviral Res. May 2006;70(1):p. A29-A30, abstract No. 11.
Leophonte, P. Antivirals for influenza. Bull Acad Natl Med. Feb. 2005;189(2):341-55.
Nguyen, et al. Triple combination of amantadine, ribavirin, and oseltamivir is highly active and synergistic against drug resistant influenza virus strains in vitro. PLoS One. Feb. 22, 2010;5(2):e9332.
Nguyen, et al. Triple combination of oseltamivir, amantadine, and ribavirin displays synergistic activity against multiple influenza virus strains in vitro. Antimicrob Agents Chemother. Oct. 2009;53(10):4115-26.
Programs and Abstracts of the 19th International Conference on Antiviral Research (ICAR). San Juan, Puerto Rico. May 7-11, 2006.
Smee, et al. Effects of double combinations of amantadine, oseltamivir, and ribavirin on influenza A (H5N1) virus infections in cell culture and in mice. Antimicrob Agents Chemother. May 2009;53(5):2120-8.

(Continued)

*Primary Examiner* — Eric S Olson
(74) *Attorney, Agent, or Firm* — Wilson Sonsini Goodrich & Rosati (57) ABSTRACT

Kits comprising an M2 inhibitor selected from amantadine and rimantadine; ribavirin, and a neuraminidase inhibitor (NAi) in an amount that is antivirally effective in the combination, an oral dosage form containing 75-250 mg of the M2 inhibitor, an oral dosage form comprising 100-400 mg of ribavirin and a neuraminidase inhibitor are provided for the treatment of influenza. Some embodiments of the kits comprise an oral dosage form containing 75-250 mg of the M2 inhibitor, an oral dosage form comprising 100-400 mg of ribavirin, and a neuraminidase inhibitor.

7 Claims, 3 Drawing Sheets

OTHER PUBLICATIONS

Nguyen et al., "Triple Combination of Amantadine, Ribavirin, and Osetamivir Is Highly Active and Synergistic against Drug Resistant Influenza Virus Straing in Vitro," PLoS One 5(2):1-12 (2010).

Nguyen et al., "Triple Comination of Oseltamivir, Amantadine, and Ribavirin Displays Synergistic Activity against Multiple Influenza Virus Strain in Vitro," Antimicrobial Agents and Chemotherapy 53(10): 4115-4126 (2009).

Hoopes et al., "Evaluation of the Contribution of Amantadine, Ribavirin, and Oseltamivir in a Triple Combination Antiviral Drug (TCAD) Regimen to Suppressing the Emergence of Resistance Using a Novel Quantitative Approach," Poster shown at $23^{rd}$ ICAR Meeting Apr. 25, 2010, http://isar.phrm.cf.ac.uk/node/69.

Nguyen et al., "Triple Combination Antiviral Drug (TCAD) Regimen Composed of Amantadine, Ribavirin, and Oseltamivir Imposes a High Genetic Barrier tot he Development of Resistance against Influenza A Viruses in Vitro," Poster shown at $23^{rd}$ ICAR Meeting, Apr. 25, 2020, http://isar.phrm.cf.ac.uk/node/69.

Gross et al., "The Triple Combination Antiviral Drug (TCAD) Regimen of Amantadine, Ribavirin, and Oseltamivir is Highly Efficacious Against Susceptible and Resistant Influenza Virus Strains in Mouse Treatment Models," Poster shown at $23^{rd}$ ICAR Meeting Apr. 25, 2010, http://isar.phrm.cf.ac.uk/node/69.

Aoki, F.Y. et al., Early administration of oral oseltamivir increases the benefits of influenza treatment, J Antimicrob Chemother 2003, 51:123-29.

Burlington, D.B. et al., Anti-influenza A activity of combinations of amantadine and ribavirin in ferret tracheal ciliated epithelium, J Antimicrob Chemother 1983, 11:7-14.

Colgan, R. et al., Antiviral drugs in the immunocompetent host: part II. Treatment of influenza and respiratory syncytial virus infections, Am Pam Physician 2003, 67(4):763-6, 675 (abstract).

De Clercq, E., Antiviral agents active against influenza A viruses, Nature Reviews, Drug Discovery 2006, 5:1015-25.

De Clercq, E., Influenza virus inhibitors available for the chemotherapy and/or chemoprophylaxis of influenza virus infections, Verh K Acad Geneeskd Belg 2006, 68(2):121-37 (Abstract).

De Clercq., E. et al., Avian influenza A (H5N1) infection: targets and strategies for chemotherapeutic intervention, Trends Pharmacol Sci 2007, 28(6):280-5.

De Jong, M.D., Oseltamivir Resistance during Treatment of Influenza A (H5N1) Infection, N Engl J Med 2005, 353:2667-72.

Galabov, A.S. et al., Rimantadine and oseltamivir demonstrate synergistic combination effect in an experimental infection with type A (H3N2) influenza virus in mice, Antiviral Chem Chemother 2006, 17:251-8.

Galagov, G.A. et al., Combined action of ribovirin and rimantadine in experimental myxovirus infection, Experientia 1976, 33:905-6.

Govorkova, E.A. et al., Neuraminidase inhibitor-rimantadine combinations exert additive and synergistic anti-influenza virus effects in MDCK cells, Antimicrob Agents Chemother 2004, 48(12):4855-63.

Hayden, F.G. et al., Combined interferon-α2, rimantadine hydrochloride, and ribavirin inhibition of influenza virus replication in vitro, Antimicrob Agents Chemother 1984, 25(1):53-7.

Hayden, F.G. et al., Combinations of antiviral agents for treatment of influenza virus infections, J Antimicrob Chemother 1986, 18(b): 177-83.

Hayden, F.G. et al., Enhancement of activity against influenza viruses by combinations of antiviral agents, Antimicrob Agents Chemother 1980, 18(4):536-41.

Hayden, F.G., Combination antiviral therapy for respiratory virus infections, Antiviral Res 1996, 29:45-8.

Hayden, F.G. et al., Intravenous ribavirin by constant infusion for serious influenza and parainfluenzavirus infection, Aniviral Ther 1996, 1:51-6.

Ilyushina N.A., et al., Combination chemotherapy, a potential strategy for reducing the emergence of drug-resistant influenza a variants, Antiviral Res 2006, 70:121-31.

Ilyushina, N.A. et al., Amantadine-oseltamivir combination therapy for H5N1 influenza virus infection in mice, Antiviral Ther 2007, 12:363-70.

Ison, M.G., et al., Therapeutic options for the management of influenza, Curr Opin Pharmacol 2001, 1:482-90.

Ison, M.G., et al., Safety and efficacy of nebulized zanamivir in hospitalized patients with serious influenza, Antiviral Ther 2003, 8(3):183-90.

Leneva, I.A. et al., The neuraminidase inhibitor GS4104 (oseltamivir phosphate) is efficacious against A/Hong Kong/156/97 (H5N1) and A/Hong Kong/1074/99 (H9N2) influenza viruses, Antiviral Res 2000, 48:101-15.

Leophonte P., Antivirals for influenza, Bull Acad Natl Med 2005, 68(2):121-137.

Lipsitch et al., Antiviral resistance and the control of pandemic influenza, PLoS Med 2007, 4(1):e15. doi:10.1371/journal.pmed.0040015.

Madren, L.K. et al., In vitro inhibitory effects of combinations of anti-influenza agents Antiviral, Chem Chemother 1995, 6(2):109-13.

Masihi, K.N. et al., Low dose oral combination chemoprophylaxis with oseltamivir and amantadine for influenza A virus infections in mice, J Chemother 2007, 19(3):295-303.

Morrison, D. et al., A randomized, crossover study to evaluate the pharmacokinetics of amantadine and oseltamivir administered alone and in combination, PLoS One 2007, 2(12):e1305.

Moscona, A Oseltamivir resistance—disabling our influenza defenses, N Engl J Med 2005, 353:2633-6.

Smee, D.F. et al., Activities of oseltamivir and ribavirin used alone and in combination against infections in mice with recent isolates of influenza A (H1N1) and B viruses, Antiviral Chem Chemother 2006, 17:185-92.

Smee, D.F. et al., Combination treatment of influenza A virus infections in cell culture and in mice with the cyclopentane neuraminidase inhibitor RWJ-270201 and ribavirin, Chemother 2002, 48:88-93.

Snyder, D.Z. et al., The triple combination indinavir-zidovudine-lamivudine is highly synergistic, Antimicrob Agents Chemother 2000, 44(4):1051-8.

Stein, D.S. et al., Oral ribavirin treatment of influenza A and B, Antimicrob Agents Chemother 1987, 8:1285-7.

Tsiodras, S. et al., Role of combination antiviral therapy in pandemic influenza, BMJ 2007, 334:293-4.

Wilson, S.Z. et al., Amantadine and ribavirin aerosol treatment of influenza A and B infection in mice, Antimicrob Agents Chemother 1980, 17(4):642-8.

Wong, S.S.Y. et al., Avian Influenza Virus Infections in Humans, Chest 2006, 129:156-68.

* cited by examiner

COMPOSITIONS AND KITS FOR TREATING INFLUENZA

This application claims benefit of priority under 35 U.S.C. §119(e) of provisional patent application 60/918,011, filed Mar. 13, 2007, provisional patent application 60/978,099, filed Oct. 5, 2007, and 60/989,790, filed Nov. 21, 2007, each of which is incorporated by reference herein in its entirety.

BACKGROUND OF THE INVENTION

The field of the invention is antiviral combinations and their use for the treatment or prophylaxis of influenza in a patient.

Four antiviral drugs are currently approved by FDA to treat acute, uncomplicated influenza. The M2 inhibitors amantadine hydrochloride (SYMMETREL®) and rimantadine (FLUMADINE®) are approved for treatment and prevention of influenza A. Both amantadine and rimantadine are provided in 100 mg tablets and 50 mg/ml syrup for oral administration. The usual adult dose for both drugs is 200 mg in two divided doses per day (BID). The pediatric dose of amantadine in patients 1-9 years of age is 4.4 to 8.8 mg/kg/day, not to exceed 150 mg per day; for rimantadine, the dose is 5 mg/kg administered once per day (QD), not to exceed 150 mg per day.

The neuraminidase inhibitors zanamivir (RELENZA®) and oseltamivir phosphate (TAMIFLU®) are approved for treatment and prevention of influenza A and B. Zanamivir is provided for oral inhalation only for use with an inhalation device. The recommended dose of zanamivir for prophylaxis and treatment of influenza is 10 mg/day QD and 20 mg/day BID, respectively. Oseltamivir phosphate is available as a capsule containing 75 mg oseltamivir for oral use, and as a powder for oral suspension, which when constituted with water as directed contains 12 mg/ml oseltamivir. The recommended dose of oseltamivir for patients over 13 years old for prophylaxis and treatment of influenza is 75 mg/day QD and 150 mg BID, respectively.

Various combinations of antiviral drugs have been proposed for treatment of influenza. U.S. Pat. No. 5,866,601 discloses combining neuramimidase inhibitor compositions with antivirals (such as amantadine, rimantadine and ribavirin). In vitro and in vivo animal model studies on the effect of various dual combinations of drugs against influenza have been reported (see e.g. including combinations of ribavirin with amantadine (Wilson et al., Antimicrob Agents Chemother (1980) 17:642-648; Hayden et al., Antimicrob Agents Chemother (1980) 18:536-41; and Burlington et al., J. Antimicrob Chemother (1983) 11:7-14), rimantadine (Hayden et al., supra; Galegov et al., Experientia (1977) 33:905-906; and Madren et al., Antivir Chem Chemother (1995) 6:109-113), peramavir (Smee et al., Chemotherapy (2002) 48:88-93), and oseltamivir (Smee et al., Antiviral Chem Chemother (2006) 17:185-92); and combinations of oseltamivir with amantadine (Ilyushina et al., Antiviral Res. (2006) 70:121-31) and rimantadine (Govorkova et al., Antimicrob Agents Chemother (2004) 48:4855-4863; Galabov et al., Antivir Chem Chemother (2006) 17:251-8; and Leneva et al., Antiviral Res (2000) 48:101-15). Several of these papers reported that combinations of ribavirin and amantadine have additive to synergistic effect against influenza virus compared to treatment with the drugs singly (see e.g. Wilson et al., supra; Hayden et al., supra; and Burlington et al., supra). In some of the studies, the combination treatments are reported to have adverse results compared to the monotherapy treatments. For example, the combination of oseltamivir and rimantadine at low concentrations of each drug was reported to result in an antagonistic interaction against influenza A virus (Govorkova et al., supra). Smee et al. (2006) reported that treatment of influenza A virus-infected mice with the combination of oseltamivir plus ribavirin was no better than ribavirin used alone, and that when the treatments were initiated three to four days post-infection, the groups treated with the combination had fewer survivors than the animals treated with ribavirin alone.

Viral resistance to the M2 inhibitors rimantadine and amantadine can emerge rapidly during treatment because certain single point mutations in the M2 protein can confer resistance to both amantadine and rimantadine. In January 2006, CDC testing revealed that a high proportion of influenza A viruses circulating in the U.S. were resistant to amantadine and rimantadine, causing the CDC to recommend against the use of these drugs for the treatment and prophylaxis of Influenza (CDC Health Alert, Jan. 14, 2006). Currently, oseltamivir is considered a frontline treatment for influenza A virus. However, oseltamivir-resistant strains have been reported (de Jong et al., N Engl J. Med. (2005) 353: 2667-72; Euro Surveill. (2005) 10(10):E051020.2) raising concerns that transmissible, pathogenic resistant strains could reduce the benefits of antiviral use in pandemic control (Lipsitch et al., PLoS Med (2007) January 23; 4(1):e15 [Epub ahead of print]). Further, oseltamivir treatment has been linked to serious neuropsychiatric events, especially in pediatric patients (see Prescrire Int. (2006) 15:182-3).

In view of the foregoing, one object of the invention is to provide improved therapeutics for treatment or prophylaxis of influenza, particularly pandemic influenza and/or strains of influenza that are resistant to an M2 inhibitor and/or a neuramimidase inhibitor.

Another object of the invention is to provide improved therapeutics for treatment or prophylaxis of influenza that prevent the generation of drug-resistant strains within a patient or population.

Another object of the invention is to provide improved therapeutics for treatment or prophylaxis of influenza that have significantly fewer or no adverse events or toxic effects compared to current monotherapies.

SUMMARY OF THE INVENTION

One aspect of the invention is a composition for the treatment or prophylaxis of influenza in a patient, said composition comprising: 10-60 weight percent (wt. %), 25-50 wt %, or 50-75 wt % amantadine or rimantadine; and 30-80 wt. %, 50-75 wt. %, or 25-50 wt. % ribaviran or viramidine, wherein the weight percents are based on the total weight of active agents in the composition. In specific embodiments, the composition further comprises 0.5-30 wt. % oseltamivir.

In one embodiment, the composition is in a formulation suitable for oral or gastric administration, such as a liquid, syrup, suspension, tablet, capsule, beads in capsules, or beads in sachets. In a specific embodiment, the composition is in a unit dosage form for oral administration comprising 25-125 mg amantadine or rimantadine and 50-200 mg ribavirin or viramidine. In a specific embodiment, the unit dosage form comprises at least 125 mg amantadine in an extended release form, and less than 200 mg ribavirin. In another embodiment the unit dosage form comprises 25-125 mg amantadine and 50-200 mg ribavirin.

In another embodiment, the composition is in a form suitable for parenteral administration, such as a lyophilized powder, which is reconstituted prior to administration, or a sterile liquid in a vial.

Another aspect of the invention is a kit for the treatment or prophylaxis of influenza in a patient comprising amantadine or rimantadine, and ribavirin or viramidine, and optionally a neuraminidase inhibitor such as oseltamivir, zanamivir, or peramivir.

In a specific embodiment, a kit is provided for the oral treatment or prophylaxis of influenza in a patient comprising a plurality of dosage forms, said plurality constituting one or more doses, each dose comprising a therapeutically or prophylactically effective amount of a combination of ribavirin and amantadine. The amantadine and ribavirin may be formulated as separate dosage forms or co-formulated as single dosage forms. The amantadine may be in an extended release form. In a specific embodiment, the amantadine and ribavirin are formulated as separate dosage forms, with each amantadine dosage form comprising 75-250 mg amantadine, and each ribavirin dosage form comprising 50-200 or 100-400 mg ribavirin. In various embodiments, the kit comprises an amantadine dosage form in a dosage strength selected from 80 mg, 180 mg, and 330 mg, and a ribavirin dosage form in a dosage strength selected from the group consisting of 115 mg, 330 mg and 660 mg. In one embodiment, each dose further comprises oseltamivir.

In another embodiment, the kit is provided for parenteral treatment of influenza in a human patient, comprising amantadine in a form suitable for parenteral administration; and ribavirin in a form suitable for parenteral administration. The amantadine may be contained in a plurality of first vials, and the ribavirin contained in a plurality of second vials. Alternatively, the amantadine and ribavirin are co-formulated and contained in a plurality of vials. The kit may further comprise oseltamivir, peramivir, or zanamivir in a form suitable for parenteral administration.

Another aspect of the invention is a method for the treatment or prophylaxis of influenza in a patient, said method comprising: administering to the patient an effective amount of a combination of three different antiviral agents having corresponding three different mechanisms of action, selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor.

In a specific embodiment, the method comprises administering to the patient an effective amount of a combination of first, second and third antiviral agents comprising: a) an M2 inhibitor selected from the group consisting of rimantadine and amantadine; b) an RNA polymerase inhibitor selected from the group consisting of ribavirin and viramidine; and c) a neuraminidase inhibitor (NAi) selected from the group consisting of oseltamivir, zanamivir, and peramivir.

In a preferred embodiment the first and second antiviral agents are administered in amounts that increase sensitivity of an influenza virus to the third antiviral agent by at least 2-fold over sensitivity of the virus to the third antiviral agent when used as monotherapy. In a specific such embodiment, the first and second antiviral agents are ribavirin and oseltamivir, and the third antiviral agent is amantadine.

In one embodiment of the method, the antiviral agents are administered to the patient by a method selected from the group consisting of orally, parenterally, by inhalation, and combinations thereof.

In a specific embodiment, the patient is administered amantadine or rimantadine in an amount to maintain a plasma concentration between 0.1 to 3.0 µg/ml, 0.1 to 1.5 µg/ml, or 0.3 to 1.5 µg/ml for at least 48 continuous hours.

In another embodiment, the patient is administered amantadine or rimantadine parenterally or orally in an amount of 5 to 500 mg/day, 20 to 250 mg/day, 100 to 800 mg/day, 100 to 600 mg/day, 200 to 700 mg/day, or 200 to 500 mg/day. When orally administered, amantadine is optionally in an extended release form.

In a further embodiment, the patient is administered amantadine by intravenous infusion at a rate of 1 to 50 mg/hr, 3 to 40 mg/hr, or 5 to 30 mg/hr for at least 48 continuous hours.

In one embodiment, the patient is administered ribavirin or viramidine in an amount to maintain a plasma concentration between 0.1 to 10.0 μg/ml, 0.5 to 8 μg/ml, 0.5 to 5.0 μg/ml, 1 to 6 μg/ml, 1 to 4 μg/ml, 2 to 6 μg/ml, 2 to 4 μg/ml, 0.01-2 μg/ml, or 0.2-2 μg/ml for at least 48 continuous hours. The patient is administered ribavirin parenterally or orally in an amount of 50 to 2000 mg/day, 50 to 1600 mg/day, 100 to 1200 mg/day, 400 to 800 mg/day, 50 to 600 mg/day, 75 to 500 mg/day, or 75 to 200 mg/day.

In a specific embodiment, the patient is administered ribavirin by intravenous infusion at a rate of 5 to 200 mg/hr, 10 to 150 mg/hr, 15 to 100, or 20 to 80 mg/hr for at least 48 continuous hours.

In a specific embodiment, wherein the patient is administered amantadine or rimantadine in one of the above-specified amounts together with ribavirin or viramidine in one of the above-specified amounts, the patient is further administered a neuraminidase inhibitor selected from the group consisting of oseltamivir, oseltamivir carboxylate, zanamivir, and peramivir, in an amount to maintain a plasma concentration of the neuraminidase inhibitor between 0.001-5 μg/ml, 0.02 to 5 μg/ml, 0.1 to 3 μg/ml, 0.1 to 1 μg/ml, 0.3 to 3 μg/ml, or 0.3 to 1 μg/ml for at least 48 continuous hours.

In a specific embodiment, the patient is administered zanamivir by intravenous infusion at a rate of 0.1 to 10 mg/hr, 0.4 to 7 mg/hr, or 1 to 5 mg/l hr for at least 48 continuous hours.

In another embodiment, the patient is administered oseltamivir by intravenous infusion at a rate of 0.1 to 20 mg/hr, 0.4 to 7 mg/hr, 1 to 7 hr, 1 to 5 mg/hr, or 2 to 7 mg/hr for at least 48 continuous hours.

In various embodiments, the patient may be administered oseltamivir parenterally or orally in an amount of 10 to 150 mg/day, 10 to 50 mg/day, 50 to 100 mg/day, 75 to 150 mg/day, 150 to 300 mg/day, 100 to 500 mg/day, or 1 to 50 mg/day.

The invention provides a first antiviral agent, a second antiviral agent and a third antiviral agent for simultaneous separate or sequential administration, wherein the three agents have corresponding three different mechanisms of action, selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor.

The invention also provides a first antiviral agent, a second antiviral agent and a third antiviral agent for combined use in therapy, wherein the three antiviral agents have corresponding three different mechanisms of action, selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor.

The invention also provides a first antiviral agent, a second antiviral agent and a third antiviral agent for combined use in the treatment and/or prophylaxis of influenza infection, wherein the three antiviral agents have corresponding three different mechanisms of action, selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor.

The invention also provides the use of a first antiviral agent, a second antiviral agent and a third antiviral agent in the manufacture of a medicament for the treatment and/or prophylaxis of influenza infection, wherein the three antiviral agents have corresponding three different mechanisms of action, selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor. As described below, the three agents may be administered separately from each or in double or triple combinations.

The invention also provides the use of an antiviral agent in the manufacture of a medicament for the treatment and/or prophylaxis of influenza infection, wherein the antiviral agent is selected from the group consisting (of influenza virus adsorption inhibitors, M2 inhibitors, IMP dehydrogenase inhibitors, RNA polymerase inhibitors, influenza-specific interfering oligonucleotides, and neuraminidase inhibitors, and wherein the medicament is prepared for administration (or is administered) to a patient in combination with two further antiviral agents, wherein the three antiviral agents have different mechanisms of action, selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor.

The invention also provides the use of a first antiviral agent in the manufacture of a medicament for the treatment and/or prophylaxis of influenza infection, wherein the medicament is prepared for administration (or is administered) to a patient in combination with a second antiviral agent and a third antiviral agent, wherein: a) the first antiviral agent is selected from the group consisting of influenza virus adsorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

The invention also provides the use of a second antiviral agent in the manufacture of a medicament for the treatment and/or prophylaxis of influenza infection, wherein the medicament is prepared for administration (or is administered) to a patient in combination with a first antiviral agent and a third antiviral agent, wherein: a) the first antiviral agent is selected from the group consisting of influenza virus adsorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

The invention also provides the use of a third antiviral agent in the manufacture of a medicament for the treatment and/or prophylaxis of influenza infection, wherein the medicament is prepared for administration (or is administered) to a patient in combination with a first antiviral agent and a second antiviral agent, wherein: a) the first antiviral agent is selected from the group consisting of influenza virus adsorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

The invention also provides the use of a first and a second antiviral agent in the manufacture of a medicament for the treatment and/or prophylaxis of influenza infection, wherein the medicament is prepared for administration (or is administered) to a patient in combination with a third antiviral agent, wherein: a) the first antiviral agent is selected from the group consisting of influenza virus adsorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

The invention also provides the use of one or more antiviral agent(s) in the manufacture of a medicament for the treatment and/or prophylaxis of influenza infection, wherein the antiviral agents have different mechanisms of action, selected from the group consisting of influenza virus adsorption inhibitor, M2 inhibitor, IMP dehydrogenase inhibitor, RNA polymerase inhibitor, influenza-specific interfering oligonucleotide, and neuramimidase inhibitor, and wherein the medicament is prepared for administration (or is administered) to a patient in combination with one or more further antiviral agents such that the patient receives three antiviral agents having different mechanisms of action selected from said group.

The invention also provides the use of an antiviral agent in the manufacture of a medicament for the treatment and/or prophylaxis of influenza infection in a patient, wherein the antiviral agent is selected from the group consisting of influenza virus adsorption inhibitors, M2 inhibitors, IMP dehydrogenase inhibitors, RNA polymerase inhibitors, influenza-specific interfering oligonucleotides, and neuraminidase inhibitors, and wherein the patient has previously been treated with at least two further antiviral agents, wherein said antiviral agents have different mechanisms of action, said different mechanisms of action being selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor.

The invention also provides the use of a first antiviral agent in the manufacture of a medicament for the treatment and/or prophylaxis of influenza infection in a patient, wherein the patient has previously been treated with a second antiviral agent and, optionally, a third antiviral agent, wherein: a) the first antiviral agent is selected from the group consisting of influenza virus absorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

The invention also provides the use of a second antiviral agent in the manufacture of a medicament for die treatment and/or prophylaxis of influenza infection in a patient, wherein the patient has previously been treated with a first antiviral agent and) optionally, a third antiviral agent, wherein: a) the first antiviral agent is selected from the group consisting of influenza virus absorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

The invention also provides the use of a third antiviral agent in the manufacture of a medicament for the treatment and/or prophylaxis of influenza infection in a patient, wherein the patient has previously been treated with a first antiviral agent and a second antiviral agent, wherein: a) the first antiviral agent is selected from the group consisting of influenza virus absorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

In these uses, the previous treatment of the patient will typically have been no more than 7 days prior to administration of said medicament (e.g. in the previous 7, 6, 5, 4, 3, 2 days, or in the previous 24 hours).

The invention also provides an antiviral agent for use in the treatment and/or prophylaxis of influenza infection, wherein the antiviral agent is selected from the group consisting of influenza virus adsorption inhibitors, M2 inhibitors, IMP dehydrogenase inhibitors, RNA polymerase inhibitors, influenza-specific interfering oligonucleotides, and neuraminidase inhibitors, and wherein the antiviral agent is administered (or is prepared for administration) with at least one further antiviral agent, wherein said antiviral agents have different mechanisms of action, said different mechanism of action being selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor.

The invention also provides a first antiviral agent for use in the treatment and/or prophylaxis of influenza infection, wherein the first antiviral agent is administered (or is prepared for administration) with a second antiviral agent and, optionally, a third antiviral agent, wherein: a) the first antiviral agent is selected from the group consisting of influenza virus adsorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuramimidase inhibitor.

The invention also provides a second antiviral agent for use in the treatment and/or prophylaxis of influenza infection, wherein the second antiviral agent is administered (or is prepared for administration) with a first antiviral agent and, optionally, a third antiviral agent, wherein: a) the first antiviral agent is selected from the group consisting of influenza virus adsorption inhibitor and M2 inhibitor; b) the second antiviral agent is selected from the group consisting of IMP dehydrogenase inhibitor, and RNA polymerase inhibitor; and c) the third antiviral agent is selected from the group consisting of interfering oligonucleotide and neuraminidase inhibitor.

The invention also provides a third antiviral agent for use in the treatment and/or prophylaxis of influenza infection, wherein the third antiviral agent is administered (or is prepared for administration) with a first antiviral agent and a second antiviral agent, wherein: a) the first antiviral agent is selected from the group consisting of influenza virus adsorption inhibitor and M2 inhibitor; b) the second antiviral agent is selected from the group consisting of, IMP dehydrogenase inhibitor, and RNA polymerase inhibitor; and c) the third antiviral agent is selected from the group consisting of interfering oligonucleotide and neuraminidase inhibitor.

BRIEF DESCRIPTION OF THE FIGURES

FIGS. 1A-4 are plan views of six different respective blister packs comprising dosage forms according to different embodiments of the present invention.

DETAILED DESCRIPTION OF THE INVENTION

The invention provides methods, uses, compositions, and kits for treatment of a human patient having an influenza virus infection or suspected of being infected with or at risk of exposure to influenza virus. The invention can be used to prevent or reduce the probability of the generation of drug resistant strains, to treat a human patient suspected of being infected with or at risk of exposure to a drug-resistant influenza virus, and to minimize side-effects and toxicity associated with monotherapy.

One aspect of the invention is a method for the treatment or prophylaxis of influenza in a patient to reduce or prevent symptoms associated with influenza virus infection. The patient can be human or any other animal susceptible to influenza infection (e.g. domestic animals such as cats and dogs; livestock and farm animals such as horses, cows, pigs, chickens, etc.). Medical care standards are used to determine that that a patient is likely infected with influenza virus or is at risk of exposure to influenza virus. The influenza virus can be an A or B virus. In specific embodiments, the virus is an influenza A virus (e.g. H1N1, H1N2, H2N2, H3N2, H5N1, H7N7, H9N2, etc.).

The method comprises administering to the patient a combination of three different antiviral agents (referred to herein as a "triple combination") having corresponding three different mechanisms of action selected from the group consisting of influenza virus adsorption inhibitor, M2 inhibitor, IMP dehydrogenase inhibitor, RNA polymerase inhibitor, influenza-specific interfering oligonucleotide, and neuraminidase inhibitor. One or more additional antiviral agents may be added to the triple combination (e.g. a fourth antiviral agent having a mechanism of action that differs from the three mechanisms of the triple combination or that is the same as one of mechanisms of triple combination). References herein to specific antiviral agents (e.g. amantadine, oseltamivir, etc.) are intended to include pharmaceutically acceptable salts of the antiviral agents (e.g. amantadine hydrochloride, oseltamivir phosphate, etc.).

Figure 5:
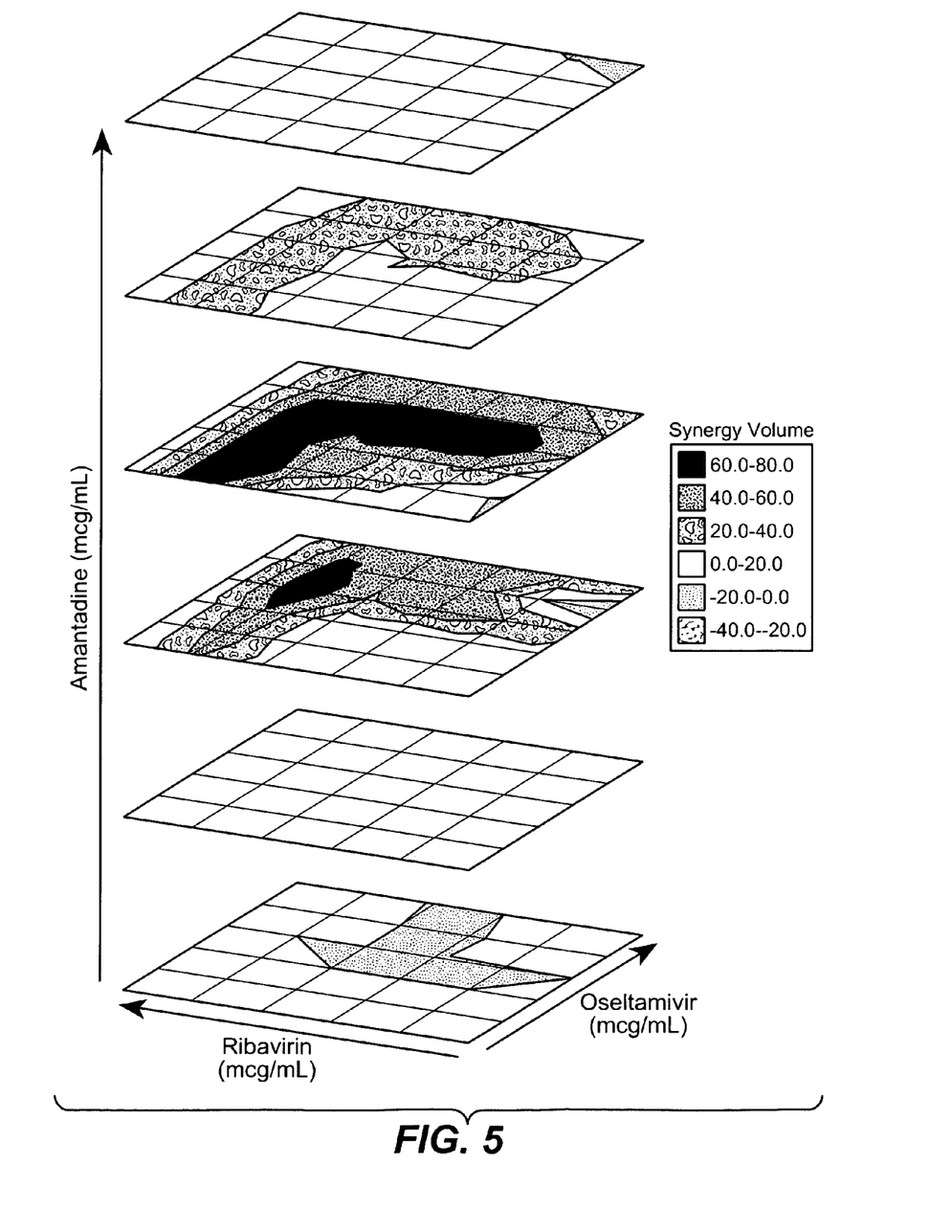
FIG. 5 is a synergy volume plot of the data generated from the experiment described in Example 1B.

The antiviral agents are preferably administered at relative ratios and dosages demonstrated to be additive or synergistic with respect to a reduction in viral load, symptoms, duration of illness, prevention of drug-resistant strains, etc. Synergy is when the efficacy of the combination is greater than the cumulative efficacy of each drug within the combination as single agents (Prichard and Shipman, Antiviral Res. (1990) 14:181-206). Methods for measuring drug synergy of antiviral agents are described in the Examples below, and are generally known in the art (see e.g. Schinazi et al., Antimicrob Agents Chemother. (1982) 22:499-507; and Prichard and Shipman, sierra; and Prichard et al., Antibicrob Agents Chemother (1993) 37:540-545; each incorporated herein by reference). FIG. 5 depicts a three-dimensional synergy plot of data obtained from the experiment described in Example 1B below; the analysis was made using methods described by Prichard et al. (1993), supra.

The use of synergistic amounts of the antiviral agents provides greater efficacy and/or allows lower amounts of one or more of the drugs to be used than that used in current monotherapy, thereby resulting in fewer side-effects for the patient and permitting the production of more treatment doses from finite amount of bulk drug. In a specific embodiment, the combination increases the sensitivity of one or more strains of an influenza virus to at least one of the antiviral agents by at least 2-fold, 5-fold, 10-fold, 20-fold, 50-fold, or 100-fold compared to the sensitivity of the virus to the drug when used as a monotherapy. For example, when a drug has an $EC_{50}$ of 1.0 μg/ml against an influenza virus when used as a monotherapy as determined by in vitro testing, and has an $EC_{50}$ of 0.01 μg/ml or less when used in combination with two other antiviral agents, the combination is said to increase the sensitivity of the influenza virus to the drug by at least 100-fold. Preferably, the sensitivity of two or all three drugs in the combination is improved by at least 2-fold, 5-fold, 10-fold, 20-fold, 50-fold, or 100-fold. Example 1B below describes an in vitro assay for determining how increases in drug sensitivity can be determined using an H3N2 influenza strain. The same assay can be used to measure drug sensitivity against other influenza strains. In the absence of synergy, combinations of antivirals may still be beneficial due to the additive contribution of each drug within the combination and the overall efficacy of the combination without added toxicity.

Use of the triple combination significantly reduces the probability of the generation of drug resistant strains compared to prior monotherapies. This is particularly advantageous in the treatment of influenza in a pandemic or localized outbreak. Further, the triple combination can be used to treat a human patient infected with or at risk of exposure to a drug-resistant influenza virus. Because rapid viral genotyping is not usually available on a real time basis to clinicians allowing rationale drug selection based on resistance profiles, the invention provides for broad and effective anti-viral coverage even in the absence of these data. In specific embodiments, the drug-resistant influenza virus is resistant to one of the drugs of the combination used. Surprisingly, treatment with the triple combination provides a greater anti-influenza effect against the drug-resistant virus than treatment that is the same except for the exclusion of the drug to which the virus is resistant as a monotherapy. Standard medical procedures are used to assess the likelihood that a patient is infected with or is at risk of exposure to a drug-resistant virus (e.g. via guidance of CDC Health Alerts, etc.).

Preferably each drug in the combination is active at a different phase in the influenza virus life cycle. For example, influenza virus adsorption inhibitors and M2 inhibitors are active at the beginning of the lifecycle; IMP dehydrogenase inhibitors and RNA polymerase inhibitors are active at the middle of the lifecycle; and interfering oligonucleotides and neuramimidase inhibitors are active at the end of the lifecycle.

Examples of influenza virus adsorption inhibitors include hemagglutinin-specific monoclonal antibodies (see e.g. Palladino et al., J. Virol. (1995) 69:2075-81), polyoxometalates (see e.g. Shigeta et al., Antimicrob Agents Chemother. (1997) 41:1423-7), sulfated polysaccharides, sialidase fusion proteins (e.g. Fludase), and O-glycosides of sialic acid (see e.g. Guo et al, Glycobiology (2002) 12:183-90). These and other influenza adsorption inhibitors are known in the art (see e.g. (*Combating the Threat Of Pandemic Influenza: Drug Discovery Approaches*, Ed. Paul F. Torrence, John Wiley And Sons Ltd (2007), incorporated herein by reference).

Examples of M2 inhibitors include aminoadamantane compounds such as amantadine (1-amino-adamantane), rimantadine (1-(1-aminoethyl)adamantane), spiro[cyclopropane-1,2'-adamantan]-2-amine, spiro[pyrrolidine-2,2'-adamantane], spiro[piperidine-2,2'-adamantane], 2-(2-adamantyl)piperidine, 3-(2-adamantyl)pyrrolidine, 2-(1-adamantyl) piperidine, 2-(1-adamantyl)pyrrolidine, and 2-(1-adamantyl)-2-methyl-pyrrolidine; and M2-specific monoclonal antibodies (see e.g. US 20050170334; and Zebedee and Lamb, J. Virol. (1988) 62:2762-72). In a preferred embodiment, one of the antiviral agents in the triple combination is amantadine or rimantadine.

Examples of IMP dehydrogenase inhibitors include ribavirin, viramidine (a prodrug of ribavirin), and merimepodib (VX-497; see e.g. Markland et al., Antimicrob Agents Chemother. (2000) 44:859-66).

As used herein, the term RNA polymerase inhibitor refers to an antiviral agent that inhibits the polymerase, protease, and/or endonuclease activity of the viral RNA polymerase complex or one of its subunits (i.e. PB1, PB2 and PA). Exemplary RNA polymerase inhibitors include antiviral nucleoside analogs such as ribavirin, viramidine, 6-fluoro-3-hydroxy-2-pyrazinecarboxamide (T-705), 2'-deoxy-2'-fluoroguanosine, pyrazofurin, 3-deazaguanine, carbodine (see e.g. Shannon et al., Antimicrob Agents Chemother. (1981) 20:769-76), and cyclopenenyl cytosine (see e.g. Shigeta et al., Antimicrob Agents Chemother. (1988) 32:906-11); and the endonuclease inhibitor flutimide (see e.g. Tomassini et al., Antimicrob Agents Chemother. (1996) 40:1189-93). In a preferred embodiment, one of the antiviral agents in the triple combination is ribavirin or viramidine.

Examples of influenza-specific interfering oligonucleotides include siRNAs (see e.g. Zhou et al., Antiviral Res. (2007) 76; 186-93), antisense oligonucleotides, phosphorothioate oligonucleotides, ribozymes (see e.g. U.S. Pat. No. 6,258,585 to Draper), morpholino oligomers and peptide nucleic acids (see e.g. Schubert and Kurreck, Handb Exp Pharmacol. (2006) 173:261-87).

Examples of neuraminidase inhibitors include oseltamivir, oseltamivir carboxylate (GS4071; see e.g. Eisenberg et al., Antimicrob Agents Chemother. (1997) 41:1949-52), zanamivir, peramivir (RWJ-27021; BXC-1812, BioCryst), 2,3-didehydro-2-deoxy-N-acetylneuraminic acid (DANA), 2-deoxy-2,3-dehydro-N-trifluoroacetylneuraminic acid (FANA), A-322278, and A-315675 (see U.S. Pat. No. 6,455,571 to Maring et al, and Kati et al., Antimicrob Agents Chemother. (2002) 46:1014-21). In a preferred embodiment, one of the antiviral agents in the triple combination is oseltamivir, peramivir, or zanamivir.

In one embodiment, the first antiviral agent is an M2 inhibitor, preferably amantadine; the second antiviral agent is an antiviral nucleoside analog, preferably ribavirin or viramidine; and the third antiviral agent is a neuraminidase inhibitor, preferably oseltamivir or zanamivir. In other embodiment, the first antiviral agent is amantadine or rimantadine; the second antiviral agent is ribavirin or viramidine, and the third antiviral agent is oseltamivir, oseltamivir carboxylate, peramivir or zanamivir.

Each antiviral agent of the combination is administered using one or more routes of administration suitable for the particular agent (e.g. orally, parenterally, by inhalation, transdermally, intranasally, gastric administration (e.g. via G-, NG-, J-, etc. feeding tubes), etc.). In various embodiments, the antiviral agents are prepared for oral administration and/or gastric administration (e.g. via feeding tubes) as liquids, syrups, suspensions, tablets, capsules, beads in capsules, or beads in sachets. In some embodiments, at least one of the antiviral agents is administered by one route of administration (e.g. parenterally), and at least one of the antiviral agents is administered by an alternate route of administration (e.g. orally or by inhalation).

In oral dosing embodiments, one or more of the antiviral agents may be provided in an immediate release (IR) or extended release (ER) form. The preparation of ER dosage forms (also referred to in the art as "controlled release", "sustained release", and "modified release" dosage forms) is well known. Suitable M2 inhibitor ER dosage forms are described in U.S. Ser. No. 11/285,905 and U.S. Ser. No. 11/399,879, both to Went et al., the contents of which are incorporated herein by reference. The antiviral agents may be administered as separate formulations, simultaneously, or sequentially. Alternatively two or more of the antiviral agents may be provided as combination compositions in single dosage forms.

When treating an established influenza virus infection in a patient presenting with symptoms of vomiting and/or diarrhea, parenteral administration is particularly preferred, as oral administration may not be effective in rapidly achieving the desired plasma concentrations of the antiviral agents. Preferably, the parenteral administration is selected from intravenous infusion, intravenous injection, or intramuscular injection. Most preferred is intravenous infusion. A preferred kit for parenteral administration comprises an M2 inhibitor (amantadine or rimantadine), an antiviral nucleoside analogue (ribavirin or viramidine), and optionally a neuraminidase inhibitor (oseltamivir, oseltamivir carboxylate, or zanamivir), which are parenterally administered together with a pharmaceutically acceptable carrier in a single pharmaceutical composition. In other embodiments, the M2 inhibitor, the antiviral nucleoside analogue, and optionally the neuramimidase inhibitor, are parenterally administered as separate dosage forms. In some embodiments, at least one of the M2 inhibitor, the antiviral nucleoside analogue, and the neuraminidase inhibitor, if present, is initially provided in the form of a lyophilized composition which is reconstituted with a pharmaceutically acceptable carrier prior to parenteral administration. In some embodiments, the M2 inhibitor, the antiviral nucleoside analogue and the neuraminidase inhibitor, if present, are each initially provided in a separate container, and thereafter are combined with a pharmaceutically acceptable carrier prior to parenteral administration. In some embodiments, one of the antiviral agents may be provided in lyophilized form which is reconstituted by a liquid formulation of one of the other antiviral agents.

The plasma concentration of each drug of the triple combination is preferably maintained between a desired Cmin and Cmax for at least 24, 48, 72, 96, 120, 144, or 168 continuous hours. Routine clinical trials are used to determine the average Cmin, Cmax, and Cmean plasma concentrations of a patient population by various dosing regimens. The duration of the therapy is typically 5-10 days for treatment, or until the virus has cleared from the patient. For prophylaxis, the daily dose of the antiviral agents administered is typically 50% that used for treatment and is administered over the course of two or more weeks, typically up to about 6 weeks or more until the risk of infection abates.

The invention is further exemplified below with respect to uses of specific antiviral agents and combinations of antiviral agents, and the dosages and concentrations at which they are used. Suitable dosages and concentrations of other antiviral agents that are not further exemplified below can be determined using information available in the literature and by routine experimentation, such as described in the examples below and known generally in the art.

In a specific embodiment of the invention, the first antiviral agent of the triple combination is amantadine or rimantadine, which is administered to the patient in an amount that maintains a plasma concentration of the amantadine or rimantadine between 0.05 µg/ml (Cmin) to 5.0 µg/ml (Cmax), preferably 0.1 to 3.0 µg/ml, more preferably 0.1 to 1.5 µg/ml, and most preferably 0.3 to 1.5 µg/ml for at least 48 continuous hours. The desired plasma concentration can be achieved by administering the amantadine or rimantadine parenterally or orally in an amount of 5 to 500 mg/day, 20 to 250 mg/day, 100 to 800 mg/day, 100 to 600 mg/day, 200 to 700 mg/day, or 200 to 500 mg/day. Particularly preferred daily oral dosages of rimantadine range from about 50-400 mg/day, 75-300 mg/day, 100-250 mg/day, or 100-200 mg/day.

In some embodiments, exemplary amantadine and rimantadine oral dosage forms contain at least about 25, 50, 75, 100, 125, 150, 175 or 200 mg per dosage form and up to about 75, 100, 125, 150, 175, 200, 225, 250, 275, 300, 350, or 400 mg per dosage form. One, two, three or four of said dosage forms may be administered one or two times per day for prophylaxis or treatment. The resulting daily doses may be at least 25, 50, 75, 100, 125, 150, 175 or 200 mg per day and up to about and up to about 75, 100, 125, 150, 175, 200, 225, 250, 275, 300, 325, 350, 400, 450, 500, 550, 600, 650, 700, 750 or 800 mg/day. In one exemplary treatment, the patient self-administers two 125 mg amantadine ER unit dosage forms (e.g. capsules or tablets) every twelve hours (i.e. BID) for a total of about 500 mg/day amantadine, typically taken in combination with ribavirin as described below. Also in this example, the prophylactic dose is one 125 mg ER dosage form BID.

For oral administration of 200 mg/day or more of amantadine or rimantadine, ER formulations are preferred as they allow for lower $C_{max}/C_{min}$ ratios, thereby optimizing the time that the M2 inhibitor concentrations remain above $ED_{50}$, while minimizing toxicity. In a preferred ER formulation, the amantadine or rimantadine has an in vitro dissolution profile of less than about 70 wt. % in one hour, less than about 90 wt. % in two hours, greater than about 40 wt. % in six hours and greater than about 85 wt. % in 12 hours, as measured using a USP type 2 (paddle) dissolution system at 50 rpm, at a temperature of 37±0.5° C. with 500 ml water as a dissolution medium. Further preferred is an ER formulation of amantadine or rinantadine with an in vitro dissolution profile of less than 20 wt % in one hour, less than about 50% in two hours, greater than about 40% in six hours, and greater than about 90% in twelve hours as measured above. This reduction in dissolution may advantageously reduce the interdose variability in plasma concentration for the active agent or improve tolerability of the active agent, especially when the administration is BID or QD. In certain embodiments, the amantadine or rimantadine is in an oral dosage form and has a Tmax of at least 4, 5, 6, 7, 8, 9, 10, 11, 12, 13, 14, 15, 16, 17, 18, 19, or 20 hours.

In a specific embodiment, the patient is administered amantadine by intravenous infusion at a rate of 1 to 50 mg/hr, 3 to 40 mg/hr, or 5 to 30 mg/hr for at least 48, 72, or 96 continuous hours.

In one embodiment of the invention, the second antiviral agent of the triple combination is ribavirin or viramidine. In a preferred embodiment, the ribavirin or viramidine is administered together with amantadine or rimantadine in the abovementioned amounts. The ribavirin or viramidine is administered to the patient in an amount to achieve a plasma concentration of 0.1 µg/ml (Cmin) to 10.0 µg/ml (Cmax), 0.5 to 8 µg/ml, 0.5 to 5 µg/ml, 1 to 6 µg/ml, 1 to 4 µg/ml, 2 to 6 µg/ml, 2 to 4 µg/ml, 0.01-2 µg/ml, or 0.2-2.0 µg/ml for at least 48, 72, or 96 continuous hours. The desired plasma concentration can be achieved by administering the ribavirin parenterally or orally in an amount of 50 to 2400 mg/day, 50 to 2000 mg/day, 50 to 1600 mg/day, 100 to 1200 mg/day, 400 to 800 mg/day, 50 to 600 mg/day, 75 to 500 mg/day, or 75 to 200 mg/day. In a preferred embodiment, the ribavirin or viramidine is administered at low daily dosages that have additive or synergistic effect when administered in combination amantadine or rimantadine and a neuraminidase inhibitor such as oseltamivir, peramivir, or zanamivir. The low dosages are typically about 10-800 mg/day, 25-600 mg/day, 50-600 mg/day, and preferably about 75-500 mg/day. In one exemplary treatment, the patient self-administers one 160 mg ribavirin unit dosage form BID for a total of 320 mg/day ribavirin.

In a specific embodiment, ribavirin or viramidine is administered orally in amounts of at least about 10, 25, 30, 40, 50, 75, 100, 125, 150, 175 or 200 mg per dosage form and up to about 150, 175, 200, 250, 300, 350, 400, 450 or 500 mg per dosage form. One, two, three or four of said dosage forms may be administered one or two times per day for prophylaxis or treatment. The resulting daily doses may be at least 10, 25, 30, 40, 50, 75, 100, 125, 150, 175 or 200 mg per day and up to about 100, 125, 150, 175, 200, 225, 250, 275, 300, 325, 350, 400, 450, 500, 550, 600, 650, 700, 750, 800, 1200, 1600, or 2000 mg/day. In one exemplary treatment, the patient self-administers 2×200 mg dosage forms BID for a total of about 800 mg per day. Also in this example, the prophylactic dose is 1×200 mg dosage form BID.

The ribavirin or viramidine (and optionally one or both of the other antiviral agents) may be administered initially in loading dose amount, and thereafter administered in a daily maintenance dose amount, wherein the loading dose amount is about 1.5 to about 3 times the daily maintenance dose amount. The loading dose may be administered by a route that is the same as or different from that of the subsequent maintenance dose. The loading dose is preferably administered parenterally or orally, and most preferably parenterally. Preferably, the loading dose is administered as an intravenous infusion, intravenous injection, or intramuscular injection. With intravenous infusion, the loading dose may be achieved by using a higher concentration of the antiviral agent in the first i.v. bag infused into the patient. Alternatively, the initial i.v. infusion bag may have the same concentration of active agents as the subsequent i.v. bags, but be administered with an increased rate of infusion (e.g. 3-6 hrs compared to 8 hrs).

In a specific embodiment, the patient is administered ribavirin or viramidine by intravenous infusion at a rate of 5 to 200 mg/hr, 10 to 150 mg/hr, 15 to 100, or 20 to 80 mg/hr for at least 48, 72, or 96 continuous hours.

In a particular embodiment of the invention, ribavirin or viramidine is administered together with amantadine and oseltamivir in the treatment of an influenza virus that is resistant to amantadine or oseltamivir monotherapy.

In one embodiment of the invention, the third antiviral agent of the triple combination is a neuraminidase inhibitor selected from the group consisting of oseltamivir, oseltamivir carboxylate, zanamivir, and peramivir. Oseltamivir and zanamivir are particularly preferred. The neuraminidase inhibitor, preferably oseltamivir or zanamivir, is administered to the patient in an amount to achieve a plasma concentration between 0.001 to 5 µg/ml, 0.02 µg/ml to 5 µg/ml 0.1 to 3 µg/ml, 0.1 to 1 µg/ml, 0.3 to 3 µg/ml, 0.3 to 1 µg/ml, 0.001 to 0.1 µg/ml, or 0.0001 to 0.01 µg/ml for at least 48, 72, or 96 continuous hours. The desired plasma concentration may be achieved by administering oseltamivir parenterally or orally in an amount of 10 to 150 mg/day, 10 to 50 mg/day, 50 to 100 mg/day, 75 to 150 mg/day, 150 to 300 mg/day, or 100 to 500 mg/day. Zanamivir is typically administered in an amount of 25-150 mg/day, preferably 40-100 mg/day.

In a preferred embodiment, the neuraminidase inhibitor is administered at low daily dosages that have additive or synergistic effect when administered in combination with amantadine and ribavirin or viramidine. In specific embodiments, synergistic effect is achieved when plasma concentrations of 0.15-1.5 µg/ml amantadine, 0.0001-0.01 µg/ml oseltamivir, and 0.6-6 µg/ml ribavirin are maintained in the patient for at least 48, 72, or 96 continuous hours. Specific dosages that achieve these plasma concentrations are determined using routine calculations and confirmed by clinical trials. The low dosages of oseltamivir are typically about 1-50 mg/day, preferably about 1-25 mg/day, and more preferably about 2.5-10 mg/day. In one exemplary treatment, a patient self-administers a unit dosage form of 25 mg oseltamivir taken QD or BID. In preferred embodiments, oseltamivir in any of the above dosages is taken in combination with any of the above-described amounts of amantadine and ribavirin. In a specific embodiment, 25 mg of oseltamivir is taken QD or BID together with 160 mg amantadine and 160 mg ribavirin (either in separate unit dosage forms, or in a combination unit dosage form) which are also taken QD or BID. In another specific embodiment, 75 mg oseltamivir is taken QD or BID together with 100 mg amantadine QD or BID and 600 mg ribavirin QD or BID.

In a specific embodiment, the patient is administered oseltamivir by intravenous infusion at a rate of 0.1 to 20 mg/hr, 0.4 to 7 mg/hr, 1 to 7 mg/hr, 1 to 5 mg/hr, or 2 to 7 mg/hr for at least 48, 72, or 96 continuous hours. The desired plasma concentration of zanamivir may be achieved by parenteral administration in an amount of 5 to 250 mg/day, 10 to 200 mg/day, or 25 to 150 mg/day. In a specific embodiment, the patient is administered zanamivir by intravenous infusion at a rate of 0.1 to 10 mg/hr, 0.4 to 7 mg/hr, or 1 to 5 mg/hr for at least 48, 72, or 96 continuous hours.

In a specific embodiment, the patient is administered oseltamivir orally in an amount of 1 to 75 mg/day, 1 to 50 mg/day, 1 to 25 mg-day, 10 to 150 mg/day, 50 to 100 mg/day, 75 to 150 mg/day, or 150 to 300 mg/day. In various embodiments, the amount of oseltamivir administered according to the present invention, if present, may be at least about 1, 2, 5, 10, 15, 20, 25, 30, 40, 50, 60, 70, 75, 80, 90, 100, 110, 120, 130, 140 or 150 mg per dosage form and tip to about 75, 80, 90, 100, 110, 120, 130, 140, 150, 160, 170, 180, 190 or 200 mg per dosage form. One, two, three or four of said dosage forms may be administered one or two times per day for prophylaxis or treatment. The resulting daily doses may be at least 1, 2, 5, 10, 15, 20, 25, 30, 40, 50, 60, 70, 75, 80, 90, 100, 110, 120, 130, 140 or 150 mg per day and up to about 75, 100, 120, 140, 150, 160, 180, 200, 220, 240, 250, 260, 280 or 300 mg per day. In one exemplary treatment, the patient self-administers a 75 mg dosage form BID for a total of about 150 mg per day; for prophylaxis the dose is 75 mg taken once every 24 hours (QD).

In addition to the triple antiviral therapy, the patient may be given an adjunctive therapy to boost natural antiviral responses. Exemplary adjunctive therapies include treatment with interferon, pegylated interferon, vitamin D (see e.g. Cannell et al., Epidemiol Infect. (2006) 134:1129-40), geranylgeranylacetone (see e.g. Unoshima et al., Antimicrob Agents Chemother. (2003) 47:2914-21), poly ICLC (see e.g. Wong et al., Antimicrob Agents Chemother. (1995) 39:2574-6), Ampligen®, and CpG-oligodeoxynucleotides (see e.g. Lopez et al., Vet Immunol Immunopathol. 2006 Nov. 15; 114(1-2):103-10). Such adjunctive therapies may be particularly beneficial for prophylaxis of influenza. However, for treatment of active influenza infections it may be desired to avoid certain adjunctive therapies (e.g. interferon treatment). Instead, the antiviral agents may be administered in conjunction with anti-immune/anti-inflammatory treatments such as corticosteroids (e.g. methylprednisolone, hydrocortisone, etc.) or statins (e.g. atorvastatin, simvastatin, etc.) to reduce the likelihood of a "cytokine storm".

Another aspect of the invention is a composition and use thereof for the treatment or prophylaxis of influenza in a human patient. In various embodiments, the compositions are prepared for oral, parenteral, or gastric administration (e.g. via feeding tubes) as liquids, syrups, suspensions, tablets, capsules, beads in capsules, or beads in sachets.

In a specific embodiment, the composition comprises amantadine or rimantadine, and ribavirin or viramidine, and optionally oseltamivir in single dosage forms for oral, gastric, or parenteral administration. In a specific embodiment, a single dosage form contains amantadine in any one of the above-specified amounts (i.e. 25, 50, 75 . . . 300 mg) in combination with ribavirin in any one of the above-specified amounts (i.e. 25, 50, 75 . . . 500 mg) and optionally oseltamivir in any one of the above-specified amounts (i.e. 25, 30, 40 . . . 200 mg). In one embodiment, the composition comprises a combination of ribavirin and ER amantadine that preferably has an in vitro dissolution profile and/or Tmax as previously described above In one embodiment, the composition comprises 10 to 60 weight percent (wt. %), 25 to 50 wt. %, or 50 to 75 wt. % amantadine or rimantadine; and 30 to 80 wt. %, 50 to 75 wt. %, or 25 to 50 wt. % ribavirin or viramidine, wherein the weight percents are based on the total weight of active agents in the composition. The composition may further comprise 0.5-30 wt. % oseltamivir. In preferred embodiments, the composition contains amounts of amantadine and ribavirin that exhibit additive or synergistic effect, as described above, when used in triple combination with a neuraminidase inhibitor such as oseltamivir, peramivir, or zanamivir, for the treatment or prophylaxis of influenza.

For parenteral administration, the composition may be in a lyophilized powder or sterile liquid form contained in a vial. The vial may be fitted with a rubber septum to allow syringe entry for reconstitution or withdrawal of the vial contents.

For oral administration, the composition may be in a unit dosage form such as a capsule or tablet. One exemplary unit dosage form for oral administration comprises 25-125 mg or 150-300 mg amantadine, optionally in ER form, and 50-200 mg ribavirin in tablets or capsules. One dosage form of the invention comprises 160 mg ER amantadine HCL and 120 mg IR ribavirin. Another exemplary dosage form is a capsule comprising 160 mg amantadine and 160 my ribavirin, and 75 mg oseltamivir.

Another aspect of the invention is kits comprising an M2 inhibitor (e.g. amantadine or rimantadine), antiviral nucleoside analogue (e.g. ribavirin or viramidine) and optionally a neuraminidase inhibitor (e.g. peramivir, zanamivir, or oseltamivir). The antiviral agents in the kit may be provided in separate dosage forms that are co-packaged together, as this can maximize the ease with which the appropriate therapeutic amount may be administered to a subject in need thereof.

In a specific embodiment, kits comprise sachets containing one or more of the active agents. The sachets may contain beads of the active agents in a unit dose quantity suitable for oral, enteral or gastric administration (e.g., via a G-, NG-, or J-tube).

When provided as a kit for oral administration, the antiviral agents may be provided in a blister pack. The individual blisters may contain one antiviral agent, or two, or all three. When provided as a blister pack, it is preferred that the antiviral agents to be provided at each dosing interval are identified separately—this may be accomplished by providing all of the dosage forms for each dose within a single blister or, if packaged in separate blisters, the blisters containing the dosage forms for each dose may be grouped or identified as a group, e.g., by the printing surrounding the blisters. Typically, the kit includes instructions for use. In some embodiments, the kit may include one or more containers of an M2 inhibitor (e.g. amantadine) and antiviral nucleoside analogue (e.g. ribavirin) in a first package, and the neuraminidase inhibitor in a second separate package. For example, the kit may comprise amantadine and ribavirin co-packaged in a first blister pack, and 75 mg oseltamivir capsules in a second blister pack. Such kits can be prepared by co-packaging blister packs of TAMIFLU® with blister packs comprising ribavirin and amantadine. In another kit of the invention, a bulk supply of TAMIFLU® (e.g. a government stockpile) is used as a source of oseltamivir. The contents of the TAMIFLU® capsules are emptied, optionally re-tested for shelf-life stability, then re-encapsulated in amounts less than 75 mg/capsule (e.g. 10, 25, 35, 50 mg), and co-packaged with additive or synergistic amounts of ribavirin and amantadine. Extending the shelf-life of oseltamivir and reducing the daily dose needed for treatment or prophylaxis of influenza has the benefit of greatly extending government stockpiles of antiviral treatment for pandemic flu.

Figure 1A:
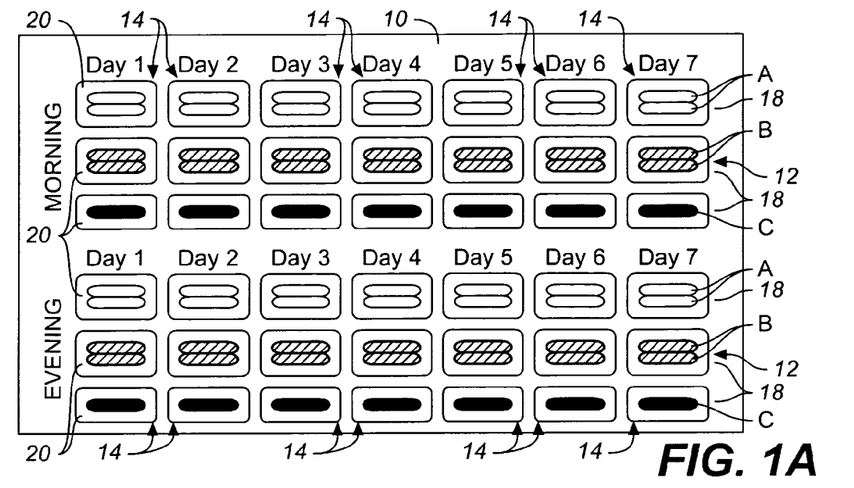
Figure 1B:
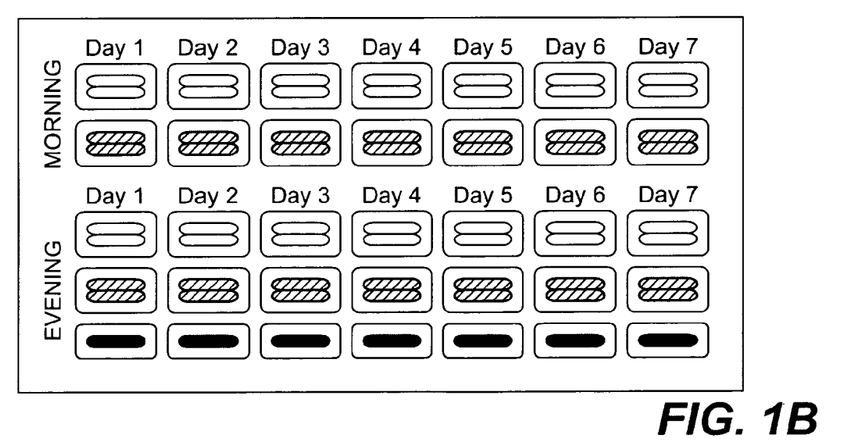
Figure 2:
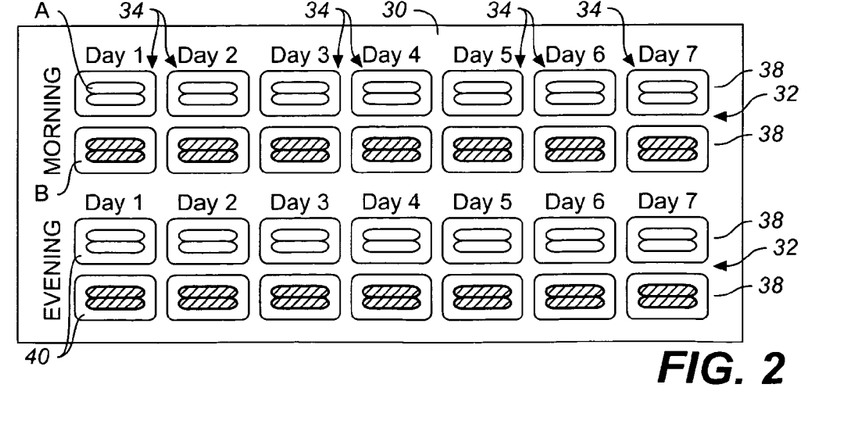

In one embodiment, a kit comprises amantadine and ribavirin provided as a plurality of separate oral dosage forms, with each amantadine dosage form comprising 75-250 mg amantadine and each ribavirin dosage form comprising 50-400 mg ribavirin. In a specific embodiment, a kit may comprise one or more blister packs comprising one or more dosage forms comprising 125 mg amantadine hydrochloride in an extended release dosage form and one or more dosage forms comprising 200 mg ribavirin. The blisters in the pack may be arranged or marked so that one of each type of dosage form should be administered once or twice per day. Alternatively, the dosage forms in the blisters may be arranged to indicate that one of the amantadine dosage forms should be administered twice per day and one of the ribavirin dosage forms should be administered once per day, or the dosage forms in the blisters may be arranged to indicate that two of the amantadine dosage forms and one of the ribavirin dosage forms should be administered once per day. Optionally, the blister pack may be configured to include one or more dosage forms comprising 75 mg oseltamivir similarly configured or marked to be administered once or twice per day. FIGS. 1 and 2 of the accompanying drawings illustrate representative configurations. Alternatively, the kit may be formatted to optimize its convenient use adjunctively with a commercially available neuraminidase inhibitor (e.g. TAMIFLU®).

In another embodiment, a kit may be provided comprising one or more blister packs, wherein each blister pack comprises one or more groups of blisters and within each group of blisters one of the blisters contains one or two tablet or capsule dosage forms comprising 60 to 300 mg amantadine in an extended release formulation and one of the blisters contains one or two tablet or capsule dosage forms comprising 25 to 200 mg ribavirin. The number of groups within a blister pack or the number of groups provided in the kit may vary from one to about 5, 7, 10, 14, 15, 20, 21, 28, 30, 40, 42 or 60. Optionally, said kit includes instructions for once or twice per day administration.

Another exemplary kit for oral administration of amantadine together with ribavirin comprises unit dosage forms of 80 mg, 180 mg, or 330 mg amantadine in immediate release or extended release form; and unit dosage forms of 330 mg or 660 mg ribavirin. In an exemplary treatment a patient is administered 660 to 2400 mg RBV and 360 to 660 mg amantadine as the first dose (e.g. Day 1 AM); thereafter (e.g. Day 2 AM to Day 10) the patient is administered 660 to 1320 mg RBV and 180 to 660 mg amantadine once daily (QD).

When provided as a kit for parenteral treatment two or more of the antiviral agents of the combination are provided in a form suitable for parenteral administration. For example, the antiviral agents may be individually formulated or co-formulated and filled into suitable containers such as syringes, ampoules, or vials. The active agents may be provided in the form of a lyophilized composition in a container, and reconstituted with a pharmaceutically acceptable carrier prior to parenteral administration. In other embodiments, the active agents may be provided in a liquid form in a container that may be administered without dilution (e.g. for i.v. or i.m.

bolus administration), or alternatively added to an i.v. infusion bag. In some embodiments, one of the antiviral agents may be provided in lyophilized form, which, prior to administration to a patient, is reconstituted with a liquid form of another antiviral agent provided in the kit. In some embodiments, an M2 inhibitor (e.g. amantadine or rimantadine), antiviral nucleoside analogue (e.g. ribavirin or viramidine), and neuraminidase inhibitor (e.g. oseltamivir, zanamivir, or peramivir), if present, are each in a separate container, and thereafter the active agents are combined with a pharmaceutically acceptable carrier prior to parenteral administration. Each container may contain a unit dose of the active agent(s), and each kit may have a sufficient number of the containers to treat an individual patient for at least 12, 24, 48, or 72 hours. The kit may have a distinctly marked container for a loading dose of one or more of the active agents with instructions indicating that the distinctly marked container is the first one used when initiating a patient's treatment. Alternatively, loading doses may be separately packaged and may have separate instructions for use. Exemplary kits for oral treatment are further detailed in Examples 5-9 below. Exemplary kits for parenteral administration are described in Example 11 below.

EXAMPLE 1A

A Dose Response Study of the Antiviral Activity of Amantadine, Oseltamivir, and Ribavirin, Singly and in Double and Triple Combinations, in A/Albany/1/98 (H3N2) Infected MDCK Cells Cultured in Flasks We performed experiments designed to evaluate the dose response antiviral activity of a combination of amantadine, oseltamivir, and ribavirin in the inhibition of A/Albany/1/98 (H3N2) viral replication. The objectives of the experiment were to demonstrate a reduction of viral load compared to no drug and synergistic effect of double and triple combinations compared to monotherapy.

The $EC_{25}$, $EC_{50}$, and $EC_{75}$ (where, e.g., $EC_{50}$, is the concentration of drug that reduces 50% of the virus at 72 hrs) for each drug were demonstrated in dose ranging studies using each drug as monotherapy. Briefly, compounds at varying doses were added to MDCK cells grown in flasks using previously described methods (Smee et al., Chemotherapy (2002) 48:88-93). Thirty minutes after the addition of the drug, viruses were added at a multiplicity of infection of 0.001 PFU per cell to each well. After ~24-78 hours, the extracellular virus medium from each well was removed, centrifuged at 3,200 g for 5 min, and titrated for virus. The results are provided in Table 1A.

TABLE 1A

| Drug | Inhibition level | In vitro C | Target serum C |
|---|---|---|---|
| Amantadine | EC25 | 0.054 µg/ml | 0.288 µm |
| Amantadine | EC50 | 0.091 µg/ml | 0.480 µm |
| Amantadine | EC75 | 0.153 µg/ml | 0.815 µm |
| Oseltamivir | EC25 | 0.025 ng/ml | 0.080 nM |
| Oseltamivir | EC50 | 0.050 ng/ml | 0.160 nM |
| Oseltamivir | EC75 | 0.075 ng/ml | 0.240 nM |
| Ribavirin | EC25 | 0.310 µg/ml | 0.760 µM |
| Ribavirin | EC50 | 0.420 µg/ml | 1.030 µM |
| Ribavirin | EC75 | 0.615 µg/ml | 1.500 µM |

The $EC_{25}$, $EC_{50}$, and $EC_{75}$ concentrations for each drug were tested singly and at all possible double and triple combinations for additive and/or synergistic effects on viral replication in tissue culture, for a total of 64 conditions tested (i.e. no drug, 9 single treatments, 27 double combination treatments, and 27 triple combination treatments). Briefly, MDCK cells were grown as monolayers in flasks, the drugs were added to the culture, and the cells were infected through the introduction of A/Albany virus at a multiplicity of infection (MOI), i.e. ratio of infectious virus particles to the number of cells being infected, of 0.001 PFU per cell. Culture was maintained for ~48 hours or until cytopathic effect was evident in monolayer. After centrifugation, supernatants were stored at −70° C. as 3×500 µl aliquots for $TCID_{50}$, PFU, and NA analysis and 1×200 µl for QPCR.

Drug combinations were determined to be synergistic if the actual inhibition of viral replication was greater than the calculated inhibition using the MacSynergy II software as described by Prichard et al. (Antimicrob Agents Chemother (1993) 37:540-545). Strong synergy was seen with double combinations of amantadine with ribavirin and amantadine with oseltamivir, at sufficiently low concentrations that will result in fewer adverse side-effects in humans. In addition, triple combinations with amantadine at $EC_{25}$ and $EC_{50}$ demonstrated a strong synergistic effect at concentrations that would minimize or avoid side-effects.

EXAMPLE 1B

A Dose Response Study of the Antiviral Activity of Amantadine, Oseltamivir and Ribavirin in Combination in A/Sydney/05/97H3N2 Infected MDCK Cells The objective of this study was to demonstrate that the triple combination of amantadine, oseltamivir and ribavirin reduces viral load compared to no drug, and exhibits a synergistic effect compared to monotherapy. The methods used were the same as those used in Example 1A, except for where noted below.

MDCK cells were grown as monolayers in 96-well plates and infected through the introduction of A/Sydney/05/97 H3N2 virus at MOI of 0.01 PFU per cell. Drugs were added at each of the 216 possible combinations at the following concentrations: amantadine at 0, 0.032, 0.1, 0.32, 1.0, and 3.2 µg/ml; oseltamivir at 0, 0.001, 0.0032, 0.01, 0.032, and 0.1 µg/ml; and ribavirin at 0, 0.032, 0.1, 0.32, 1.0, and 3.2 µg/ml.

The three-dimensional analytical method described by Prichard and Shipman (1990), supra, and Prichard et al. (1993), supra was used to visualize the data as depicted in FIG. 5, above. Amantadine in double combination with ribavirin or oseltamivir demonstrated synergy, whereas the double combination of oseltamivir with ribavirin was not synergistic. Synergy was seen at the following concentration ranges: amantadine at 0.1-1 µg/ml, ribavirin at 0.032-1.0 µg/ml, and oseltamivir at 0.001-0.032 µg/ml. These concentrations correspond to human daily dosages of approximately 50-200 mg amantadine, 200-600 mg ribavirin, and 2.5-25 mg oseltamivir. Synergy was not demonstrated in amantadine concentrations above 1 µg/ml due to the limit of the detection assay (i.e. there was complete inhibition of viral load).

The experiment further demonstrated the synergistic interactions of the three drugs when used in combination. Sensitivity of the virus to each drug when used in triple combination was improved by 10- to over 100-fold compared to each drug used as monotherapy. For example, monotherapy with amantadine at a concentration of 1 µg/ml resulted in approximately a 60% reduction in viral load, whereas approximately the same reduction in viral load was achieved with amantadine at 0.1 µg/ml in combination with 0.01 µg/ml oseltamivir and 0.32 µg/ml ribavirin, demonstrating a 10-fold increase in sensitivity to amantadine. Monotherapy with oseltamivir at a concentration of 0.1 µg/ml resulted in approximately a 50% reduction in viral load, whereas oseltamivir at 0.001 µg/ml in combination with 0.32 µg/ml amantadine and 0.32 µg/ml ribavirin resulted in approximately a 65% reduction in viral load, demonstrating more than a 100-fold increase in sensitivity to oseltamivir. Monotherapy with ribavirin at concentrations of 1 µg/ml and 3.2 µg/ml resulted in approximately 10% and 95% reductions in viral load, respectively, whereas ribavirin at 0.032 µg/ml in combination with 0.32 µg/ml amantadine and 0.01 µg/ml oseltamivir resulted in approximately a 95% reduction in viral load, demonstrating, a 100-fold increase in sensitivity to ribavirin.

EXAMPLE 1C

Study to Determine the Efficacy of Mono and Combination Therapy in an In Vitro Kinetic Assay The objective of this study was to assess the antiviral efficacy of amantadine, oseltamivir, and ribavirin as single agents and in combination in an in vitro kinetic model of Influenza A/Victoria/3/75 (H3N2) virus infection. Efficacy was assessed by reduction in viral load, as measured by CCID50 and qPCR, and inhibition of viral cytopathic effect (CPE), as determined by visual inspection. A secondary objective was to determine the optimal infectious dose and the appropriate dosing ranges for each drug as single agents and the combination.

Treatment groups are outlined in Table 1C. Each group was tested in duplicate, and in both MDCK and SIAT-1 cell lines.

TABLE 1C

| Study Design | | | | |
|---|---|---|---|---|
| Group[a] | Treatment | Amantadine (μg/mL) | Oseltamivir (μg/mL) | Ribavirin (μ/mL) |
| Single-Agent Treatment Groups | | | | |
| 1 | Placebo | — | — | — |
| 2 | Amantadine (0.15) | 0.15 | | |
| 3 | Amantadine (0.5) | 0.5 | | |
| 4 | Amantadine (1.5) | 1.5 | | |
| 5 | Oseltamivir (0.0001) | | 0.0001 | |
| 6 | Oseltamivir (0.001) | | 0.001 | |
| 7 | Oseltamivir (0.01) | | 0.01 | |
| 8 | Ribavirin (0.6) | | | 0.6 |
| 9 | Ribavirin (2.0) | | | 2.0 |
| 10 | Ribavirin (6.0) | | | 6.0 |
| Combination Treatment Groups | | | | |
| 11 | Combo (0.15/0.0001/0.6) | 0.15 | 0.0001 | 0.6 |
| 12 | Combo (0.5/0.001/2.0) | 0.5 | 0.001 | 2.0 |
| 13 | Combo (1.5/0.01/6.0) | 1.5 | 0.01 | 6.0 |

[a]Each group was tested in duplicate, and in both MDCK and SIAT-1 cell lines.

MDCK and SIAT-1 cells were seeded into T25 flasks at a cell density of $4\times10^5$ cells/mL, in a total of 5 mL, in growth media. Cells were allowed to adhere to the flasks overnight, and the next day the flask were inspected to verify that cells were ~70% confluent. Cells were washed once with 5 mL infection media with or without drugs.

At T=0, flasks were infected with A/Influenza/3/7S (H3N2), at an infectious dose of $\sim10^1$ CCID50/ml. After 2 hours, the media was removed and the cells were washed once with 5 mL infection media with drug. The wash media were discarded and 5 mL of fresh infection media with drug was added.

At 24 hours, the flasks were removed from the incubator and were visually inspected for CPE. CPE, an indication of cell viability, was qualitatively assessed by scoring the flasks on a scale of 0 to 4, with 4 being the maximum CPE. Scoring is an estimation of % viability. A flask that is 100% dead is scored a 4. A flask that is 75% dead is scored at 3, 50%=2, 25%=1, and 0%=0. The media was then completely removed from the flasks and an aliquot was taken and frozen for subsequent viral load quantitation by CCID50 analysis. The cell monolayer was washed twice with 5 mL infection media with or without drugs, and 5 mL of fresh infection media with or without drug was added. The flasks were then returned to the incubator. At T=48, 72, 96, 120, 144, and 168 hours, the procedure was repeated. CPE assessment was performed and samples for viral load quantitation were collected for each regimen at each time point.

After the last time point, all the viral load samples were thawed and the viral load for each time point was determined by CCID50 analysis. MDCK cells were seeded in 384-well plates at $4\times10^5$ cells per ml with a volume of 50 mcL per well. Cells were allowed to adhere overnight. 50 μl of serially diluted virus was then added to the plate, and the plates were returned to the incubator. Plates were removed from the incubator on Days 3 and 6 and visually scored for CPE. After 6 days, the plates were frozen at −80 C in preparation for sanger sequencing.

CCID50, defined as the dose at which 50% of wells are infected, is calculated using the Karber calculation (Karber, 1931), given by the equation: log CCID50=L−d(S−0.5), where: L=log of the lowest dilution used in the test; d=difference between log dilution steps; and S=sum of proportion of "positive" tests (i.e. cultures showing CPE)

In the absence of drugs, the placebo arms produced a peak viral titer at 48 hours post infection in both the SIAT-1 and MDCK cell lines. Peak viral titers were similar for both SIAT-1 and MDCK cell lines, with the SIAT-1 cells producing 6.75 $\log_{10}$CCID50/0.05 mL in a 24 hour period measured at 48 hours post infection, and the MDCK cells producing 6.25 $\log_{10}$ CCID50/0.05 mL. The virus appeared to replicate faster in SIAT than MDCK cells; at 24 hours post infection, the viral titer was 4 $\log_{10}$CCID50/0.05 mL for SIAT and 2.25 $\log_{10}$CCID50/0.05 mL for MDCK cells. After reaching the peak, virus production dropped in both cell lines. Presumably, the drop in viral titer is due to all the cells having been infected and killed by the infection.

There was a good correlation between viral load and cell viability, with all the cells dying concurrent with the peak viral titer or shortly thereafter. For instance, for SIAT cells the peak viral load for the placebo group occurred at 48 hours, and complete cell death (0% cell viability) occurred at 48 hours; for MDCK cells the peak viral load occurred at 48 hours, and complete cell death occurred at 72 hours.

Treatment with the drugs as single agents gave a dose-dependent inhibition of viral load at 24 hours in both SIAT and MDCK cells. At the 24 hour time point, each drug as single agent at the high dose reduced viral load by 34 logs compared to the placebo group in SIAT cells and by 2 logs in MDCK cells. For all three drugs as single agents, the inhibition seen at the 24 hour time point was not sustained, and high viral titer can be detected at later time points. Thus, none of the single agent treatment regimens succeeded in fully inhibiting virus replication, although in all cases single agent treatment delayed the peak of viral production by 24 to 48 hours compared to placebo.

Cell viability data for the single agent regimens were consistent with the viral load data: single agent treatment was able to delay but not inhibit cell mortality. In SIAT cells, all single agent groups had complete cell mortality at 72 hours, with the high dose of each drug delaying cell death by 24 hours as compared to placebo. In MDCK cells, single agent treatment delaying cell death by a maximum of 48 to 72 hours compared to placebo. In terms of cell viability, the best single agent regimen was the 0.5 µg/mL dose of amantadine, where substantial cell death was not seen until 144 hours post infection.

Combination regimens also showed a dose dependence inhibition of virus replication. In SIAT cells, the low dose combination group delayed peak virus production by 24 hours compared to placebo, and the mid dose combination group delayed peak virus production by 48 hours. In both groups, virus production reached relatively high titers of 6.1 and 4.9 $\log_{10}$ CCID50/0.05 mL for the low and mid dose, respectively, albeit the viral load as a function of time was synergistically reduced greater than 2-fold at all times measured. The high dose combination group, however, completely inhibited virus production to undetectable levels up to the last time point taken at 168 hours post infection. Consistent with the complete inhibition of virus production, cells in the high dose combination group were also completely protected from cell death up to the last time point measured at 168 hours post infection. Given the fact that both SIAT and MDCK cells were 100% viable under this regimen throughout the entire course of the study, it can be concluded that the combination of all three drugs at the high dose tested was not cytotoxic, and that inhibition of virus production was due to the synergistic antiviral effects of the drugs in the combination and not an artificial consequence of cytotoxicity. The low and mid combination doses delayed cell death by 24 and 96 hours in SIAT cells, respectively, and by 72 and 96 hours in MDCK cells, respectively. Moreover, at these low viral replication rates, the triple combination completely suppresses the formation of resistance.

Hence, triple combinations can lead to a synergistic reduction in the rate of influenza viral growth and resistance. More specifically, in using an M2 inhibitor (e.g., amantadine), a neuraminidase inhibitor (e.g., oseltamivir, zanamivir) and a replication inhibitor (e.g., ribavirin), there is a greater than 2-fold synergistic reduction in growth rate over die concentration ranges of amantadine at 0.15-1.5 μg/ml, oseltamivir at 0.0001-0.01 μg/ml and ribavirin at 0.6-6 μg/ml.

EXAMPLE 2

Effect of Triple Combinations of Amantadine, Oseltamivir, and Ribavirin on Wild Type H3N2 Influenza in the Hollow Fiber System We designed this experiment to test the effect of the triple combination of amantadine, oseltamivir, and ribavirin on virus replication in the hollow fiber model using previously described methods (Drusano et al., Antimicrob Agents Chemother (2002) 46:464-470). The drugs, singly and in combination, were delivered at steady state concentrations by continuous infusion at steady-state for 168 hours. Briefly, $10^8$ MDCK cells were grown in hollow fibers and infected through the introduction of $10^2$ influenza virus infected cells, applied in cell culture media in a dual reservoir hollow fiber system. A wild type A/Albany (H3N2) strain was tested. The culture was maintained for 168 hours. At T=24, 48, 72, 96, 120, 144, and 168 hours post-infection, samples were removed from the hollow fiber and titrated to determine viral titer. In the drug side of the hollow fiber, twelve independent experiments were conducted to test the drug combinations and concentrations shown in Table 2:

TABLE 2

| | Drug | | |
|---|---|---|---|
| Arm | Amantadine (μg/mL) | Oseltamivir (ng/mL) | Ribavirin (μg/mL |
| 1 | 0 | 0 | 0 |
| 2 | 0.1 | | |
| 3 | 1.0 | | |
| 4 | | 1 | |
| 5 | | 10 | |
| 6 | | | 0.5 |
| 7 | | | 5 |
| 8 | 0.1 | 1 | 0.5 |
| 9 | 0.1 | 10 | 5 |
| 10 | 1 | 1 | 0.5 |
| 11 | 1 | 10 | 0.5 |
| 12 | 1 | 10 | 5 |

Samples were removed from the hollow fiber at various time points to determine the number of infectious virus. The viruses from various time points were also sequenced by Sanger method to determine the sequence of the NA, HA, and M2 genes. A reduction in sequence variation with combination treatment compared to treatment with single drugs demonstrates that triple combinations inhibit the generation of resistant mutants to any one of the drugs.

Amantadine alone had negligible effect at low dose and a 2-3 log reduction in titer at 48 hours at high dose; oseltamivir alone had ~1 log reduction at both doses; and ribavirin alone had negligible effect at low dose and ~3 log reduction at 48 hours at high dose. The combination of all three drugs at low doses resulted in ~8 log reduction in titer at 48 hours, a 4-log synergistic reduction in viral growth. The combination of all three drugs at high doses resulted in a synergistic and complete inhibition (i.e. >8 logs) at all time points. The triple combination thus demonstrated synergism at the following concentrations: amantadine at 0.1-1 μg/ml, oseltamivir at 0.001-0.01 μg/ml, and ribavirin at 0.5-5 μg/ml. These concentrations correspond to human daily dosages of approximately 50-700 mg amantadine, 200-2500 mg ribavirin, and 2.5-10 mg oseltamivir.

In addition, the monotherapy arms for amantadine and oseltamivir resulted in appreciable formation of M2 and NA drug resistance, whereas the triple high dose arm did not.

EXAMPLE 3A

Effect of Triple Combinations of Amantadine, Oseltamivir, and Ribavirin on Treatment of Influenza in Mice We designed this experiment to determine the effects of the triple combination of amantadine, oseltamivir, and ribavirin in a mouse model of influenza infection.

Female mice (17-18 g) were anesthetized with ketamine (100 mg/kg) by intraperitoneal (i.p.) injection. Alzet osmotic pumps containing amantadine were inserted surgically by subcutaneous route in the backs of mice approximately 12 hours prior to virus challenge. At the time of infection, mice were again anesthetized with ketamine. They were infected intranasally (i.n.) with approximately $2\times10^4$ cell culture infectious doses ($CCID_{50}$) of A/Victoria/3/75 (H3N2) virus per mouse in a 90-μl inoculum volume. The first oral treatments (by gavage) with oseltamivir and ribavirin were given shortly before infection and then continued once a day for 7 consecutive days (at 12 hour intervals). There were 20 placebo-treated animals that received water by oral gavage and initially 12 mice per drug-treated group. The mice were held 21 days to observe for death, and were weighed as a group every other day.

Amantadine was administered by Alzet Pump at 3 mg/ml or 10 mg/ml, to deliver 4 mg/kg/day or 13 mg/kg/day, respectively; oseltamivir was administered at 30 mg/kg/day or 10 mg/kg/day by oral gavage; and ribavirin was administered at 7 mg/kg/day or 21 mg/kg/day by oral gavage. The drugs were administered as monotherapy and in the six possible triple combinations.

All monotherapy treatments were highly effective against the infection in preventing death except for amantadine at 3 mg/ml and ribavirin at 7 mg/kg/day. The times to death were significantly increased at these doses, and the 27% survival rate (3 survivors out of 11) with 3 mg/ml of amantadine was significantly different from the placebo control.

All combinations therapies prevented mortality by 90-100%. This was not unexpected, based upon the fact that the oseltamivir monotherapy by itself provided a survival benefit of 92-100% at 10 and 30 mg/kg/day, and oseltamivir at these effective doses was a component of all of the combinations. The 10 mg/ml dose of amantadine was likewise 92% protective, so combinations with this agent would likewise be highly protective.

Amantadine at 3 mg/ml and ribavirin at 7 mg/kg/day had enough of the mice die in these groups to show delays in death that differed from the placebo control. The other dose(s) of each compound were highly protective. The compounds used in combination showed death patterns similar to the two doses of oseltamivir or the 10 mg/ml dose of amantadine.

The fact that all triple combination regimens were equal to or better than all of the monotherapy regimens suggests that the three drugs were not antagonistic in combination at the doses tested. If there were significant antagonism between any of the three drugs, it is expected that the triple combination would yield lower efficacy than monotherapy.

Overall, the survival data was not useful in assessing the benefit achieved by using the drugs in combination. However, body weight data proved to be useful in assessing benefit of the compounds in combination. The infection caused severe drops in body weight in the placebo group. Weight loss during the infection was minimal in the 10 mg/ml amantadine group, but weight loss was more substantial in the other five monotherapy groups (i.e. amantadine at 3 mg/ml, oseltamivir at 10 or 30 mg/kg/day, and ribavirin at 7 or 21 mg/kg/day). Using the UK/EU mortality criteria for animal studies (death=20% weight loss), we found that 10 mg/kg/day oseltamivir protected 40% of the mice, amantadine at 3 mg/ml protected 10%, and ribavirin at 7 mg/kg/day protected 0%. When used as a triple combination at the same drug concentrations, 100% of the mice were protected. Because amantadine at 10 mg/ml was highly protective as a monotherapy; there was not a great deal of difference in weight between the monotherapy compared to the combinations, but there was still a difference that favored the combination as being superior. Resistance formation in the triple arms was much less than recorded in the monotherapy arms (0 vs. 2%).

These results demonstrated that the triple combination containing amantadine, oseltamivir, and ribavirin was effective in providing both efficacy and resistance benefit to mice infected with an influenza A (H3N2) virus.

EXAMPLE 3B

Effect of Triple Combinations of Amantadine, Oseltamivir, and Ribavirin on Treatment of Influenza in Mice The above experiment was repeated except that initiation of treatment did not begin until 24 or 48 hours after the mice were infected with the virus, and the following drug concentrations were used: amantadine at 28 mg/kg/day, oseltamivir at 10 mg/kg/day, and ribavirin at 40 mg/kg/day.

In the study where treatment was initiated 24 hours after infection, by day 9 post infection both the amantadine monotherapy and the oseltamivir monotherapy groups had 100% mortality (using the UK/EU mortality criteria); the ribavirin monotherapy group had 20% survival; and the triple combination therapy group had 90% survival.

In the study where treatment was initiated 48 hours after infection, by day 9 all groups had more than 20% weight loss. However, the triple combination therapy group had the least amount of weight loss at approximately 22%; the ribavirin monotherapy group had about 26% weight loss; and the amantadine monotherapy and oseltamivir monotherapy groups had nearly 35% weight loss each. By day 13, all treatment groups had started gaining weight, but the weight gain in the triple combination therapy group was significantly higher—the animals in this group were approximately 90% of their original weight. In comparison, the animals in the ribavirin monotherapy group were approximately 80% of their original weight, and the animals in the oseltamivir monotherapy and amantadine monotherapy groups fared no better than the untreated controls (approximately 65-70% of their original weight).

EXAMPLE 4

A Dose Response Study of the Antiviral Activity of Amantadine, Oseltamivir and Ribavirin in Combination in H5N1 Infected MDCK Cells Cultured in Flasks We designed this experiment to evaluate the dose response antiviral activity of a combination of amantadine, oseltamivir, and ribavirin in the inhibition of A/Indonesia/05/2005 (H5N1) and A/Vietnam/1204/2004 (H5N1) viral replication and the generation of drug resistant mutants. The objectives of the experiment are to demonstrate a reduction of viral load compared to no drug and synergistic effect of combination compared to monotherapy.

MDCK cells are grown as monolayers in 96-well plates. At T=0, 150 μL of virus at 20 TCID50/mL is added to cells. Shortly thereafter, 50 μL of drug, either alone or in combination, is added to the wells to give the indicated final concentrations. The drugs are tested at the following concentrations in monotherapy: amantadine at 0.00032, 0.001, 0.0032, 0.01, 0.032, 0.1, 0.32, 1, 3.2, 10, 32 and 100 μg/ml; oseltamivir at 0.0001, 0.00032, 0.001, 0.0032, 0.01, 0.032, 0.1, and 0.32, 1.0, 3.2, 10, 32 μg/ml; and ribavirin at 0.00032, 0.001, 0.0032, 0.01, 0.032, 0.1, 0.32, 1, 3.2, 10, 32 and 100 μg/ml μg/ml. Six doses of each drug are tested in the combination: amantadine at 0, 0.01, 0.032, 0.1, 0.32, and 1.0 μg/ml; oseltamivir at 0, 0.00032, 0.001, 0.0032, 0.01, 0.032 μg/ml; and ribavirin at 0, 0.032, 0.1, 0.32, 1, and 3.2 μg/ml.

At T=72 hours, 100 μL of supernatant from each well of duplicate samples is pooled and frozen for TCID50 analysis. The remaining cell monolayer is assayed for cell viability by MTS staining.

EXAMPLE 5

A Kit of Extended Release Amantadine Hydrochloride, Ribavirin and Oseltamivir Phosphate With reference to FIG. 1A, a blister pack (10) according to the present invention is arranged to provide a plurality of rows (12), each row (12) comprising a plurality of doses (14). In the present example, there are two such rows (12), each row comprising seven doses, although the number of rows or doses may be varied as convenient.

Each dose comprises a plurality of different kinds of dosage form, which are grouped together by type in separate blisters (20) within each row to form sub-rows (18). A first kind of dosage form (A) contains amantadine, a second kind (B) contains ribavirin, and a third kind (C) contains oseltamivir. The different kinds of dosage forms for a given dose are grouped together in this manner to facilitate adherence to a prescribed dosing regimen. In this example, a single dose comprises two amantadine capsules (A), two ribavirin capsules (B) and one oseltamivir capsule (C), although the number of dosage forms of each kind for each dose may also vary as required. The blister pack shown in FIG. 1A is configured for convenient BID dosing of each of the active agents over a seven day period. The blister pack shown in FIG. 1B is the same as that shown in FIG. 1A except that the oseltamivir is dosed QD.

The amantadine capsules (A) of this example each contain 125 mg amantadine hydrochloride in an extended release form (e.g. as prepared according to U.S. Ser. No. 11/285,905) and are disposed in each of the blisters (20) of the first and fourth sub-rows (18), although each capsule may contain more or less amantadine or a different salt form of amantadine as desired.

The ribavirin capsules (B) of this example each contain 200 mg ribavirin in an immediate release form, e.g., Ribavirin USP Capsules (Schering) and are disposed in each of the blisters (20) of the second and fifth sub-rows (18), although each capsule may contain more or less ribavirin as desired.

The oseltamivir capsules (C) of this example each contain 75 mg oseltamivir, e.g., TAMIFLU™ (Roche Pharmaceuticals) and are disposed in each of the blisters (20) of the third and sixth sub-rows (18), although each capsule may contain more or less oseltamivir as desired.

The blister pack also comprises instructions indicating a typical adult dosage of two amantadine capsules, two ribavirin capsules and one oseltamivir capsule twice per day. It will be appreciated that the blister pack of this example contains dosage forms sufficient for one week of dosing, comprising 28 capsules containing 125 mg amantadine hydrochloride, 28 capsules containing 200 mg ribavirin and 14 capsules containing 75 mg oseltamivir phosphate. Thus, the relative percentage of each active agent per daily dose is 35 wt. % amantadine hydrochloride, 55 wt. % ribavirin and 10 wt. % oseltamivir phosphate.

EXAMPLE 6

A Kit of Amantadine Hydrochloride, Ribavirin and Oseltamivir Phosphate

A blister pack similar to the blister pack of Example 5 is configured to provide two rows (12) of three sub-rows (18) of seven blisters (20) per row. Two tablets or capsules of 100 mg amantadine hydrochloride (A) in an immediate release form, e.g., Symmetrel™ (Endo Pharmaceuticals or Novartis) are packaged in each of the blisters (20) of the first and fourth sub-rows (18). Two capsules of 200 mg ribavirin in an immediate release form, e.g., Ribavirin USP Capsules (Schering) are packaged each of the blisters (20) of the second and fifth sub-rows. One capsule of 75 mg oseltamivir, e.g., Tamiflu™ (Roche Pharmaceuticals) is packaged in each of the blisters (20) of the third and sixth sub-rows. The blister pack also comprises instructions indicating a typical adult dosage of two amantadine tablets or capsules, two ribavirin capsules and one oseltamivir capsule twice per day. The blister pack contains dosage forms sufficient for one week of dosing.

EXAMPLE 7

A Kit of Extended Release Amantadine Hydrochloride and Ribavirin

With reference to FIG. 2, a different blister pack (30) according to the present invention comprises two rows (32), each of two sub-rows (38) of seven blisters (40) per row to provide two rows of seven doses (34) per row. Each dose (34) comprises two different active agents, amantadine (A) and ribavirin (B), contained in different respective types of dosage form. Each dosage form type for each dose (34) is disposed in a separate blister (40). The amantadine (A) and ribavirin (B) dosage forms for each dose (34) are grouped together to facilitate adherence to the dosing regimen.

In this example, each dose (34) comprises two amantadine capsules (A) and two ribavirin capsules (B). Two capsules (A) of 125 mg amantadine hydrochloride in an extended release form (prepared according to U.S. Ser. No. 11/285,905) are packaged in each of the blisters (40) of the first and third sub-rows (38). Two capsules of 200 mg ribavirin (B) in an immediate release form, e.g., Ribavirin USP Capsules (Schering) are packaged each of the blisters (40) of the second and fourth sub-rows (38).

The blister pack (30) also comprises instructions indicating a typical adult dosage (34) of two amantadine extended release capsules (A) and two ribavirin capsules (B) twice per day (BID). The blister pack contains dosage forms sufficient for one week of dosing. The kit may be used in conjunction with a separately packaged neuraminidase inhibitor such as oseltamivir or zanamivir. Optionally therefore, said instructions may include a further instruction to co-administer one capsule of 75 mg oseltamivir, e.g., Tamiflu™ (Roche Pharmaceuticals) (not shown) once or twice per day in conjunction with the amantadine and ribavirin dosage forms. Optionally, the oseltamivir or zanamivir is provided to the subject separately from the kit as an additionally prescribed medicine.

EXAMPLE 8

A Kit of Extended Release Amantadine Hydrochloride, Ribavirin and Oseltamivir

Figure 3A:
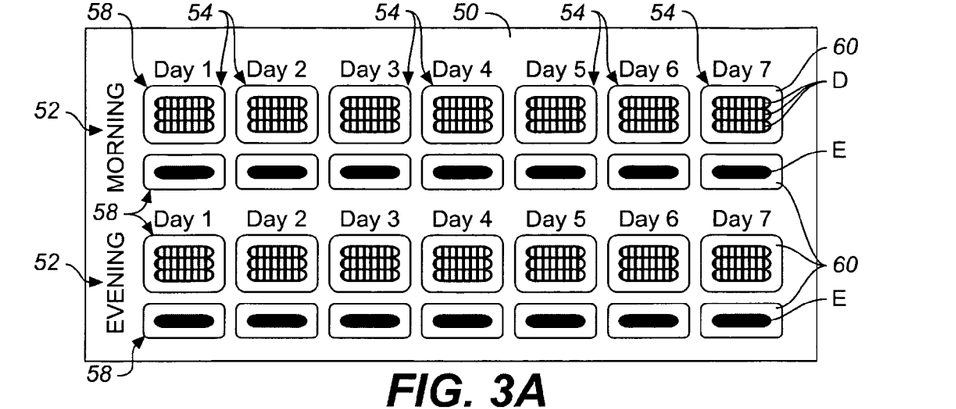

With reference to FIG. 3A, another kit for administering a combination of amantadine chloride, ribavirin and oseltamivir comprises a blister pack (50) which defines two rows (52) of blisters, each row (52) comprising two sub-rows (58) of seven blisters (60) each to define seven doses (54) per row. The rows (52) serve to group together two different types of dosage form (D, E) required for each dose (54). Each dose (54) comprises a plurality of capsules of one type (D) and one capsule of another type (E).

In the present example there are three capsules of the one type (D) per dose, but fewer or more such capsules may be used as required. Said capsules of the one type (D) comprise ribavirin and amantadine hydrochloride, in which the amantadine hydrochloride is provided in an extended release formulation, and the ribavirin is in an immediate release formulation, the two formulations being co-encapsulated.

Figure 3B:
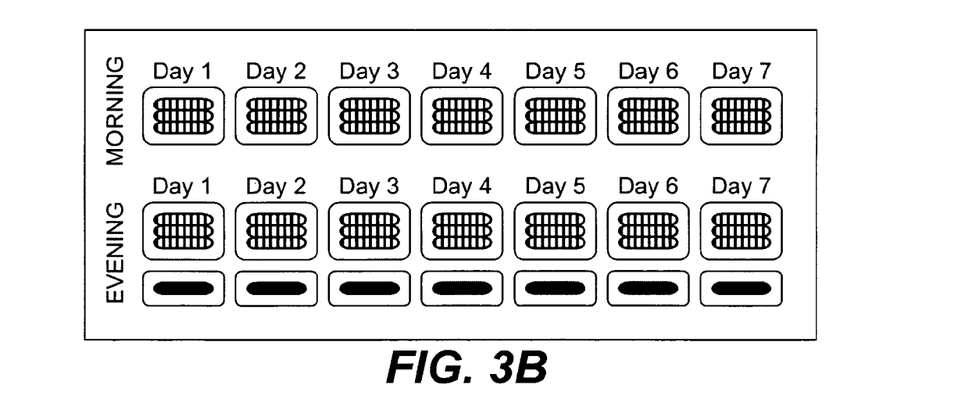

The capsules of the other type (E) comprise oseltamivir and are grouped with the amantadine—ribavirin capsules (D) to facilitate adherence with the prescribing instructions. More than one capsule of the other type (E) per dose (54) may be used if desired. The blister pack (50) of this example is thus configured for BID dosing of the active ingredients over a seven day period. The blister pack shown in FIG. 3B is the same as that shown in FIG. 3A except that the oseltamivir is dosed QD.

EXAMPLE 9

Figure 4:
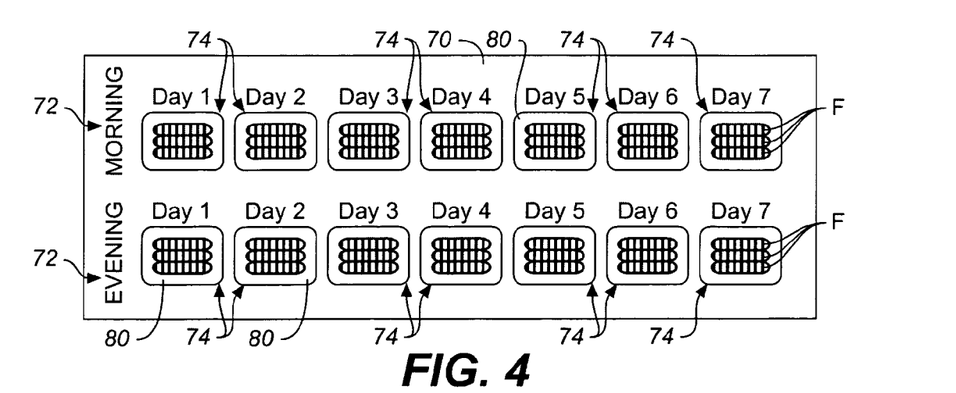

A Kit of Extended Release Amantadine Hydrochloride, Ribavirin and Oseltamivir A different blister pack (70) according to the present invention is shown in FIG. 4. Said blister pack (70) defines two rows (72) of blisters (80) in a manner similar to Examples 5-8 above. In this example however, there are no sub-rows, each row comprising a single line of seven blisters (80), each of which blisters accommodates a plurality of dosage forms (F) all of the same type, such that within each blister are sufficient dosage forms (F) to form a single dose (74). Each row (72) thus provides seven doses (74).

Each dosage form (F) in this example comprises amantadine hydrochloride in an extended release form, ribavirin and optionally oseltamivir.

The blister pack (70) is thus configured for BID dosing of each of the active agents over a seven day period. Such a kit could be used alone, especially where the dosage form comprises amantadine, ribavirin and oseltamivir, or in conjunction with a separately packaged neuraminidase inhibitor, e.g., oseltamivir.

EXAMPLE 10

Multiple Dose Safety Study in Flu Patients with an ER Amantadine, ER Oseltamivir, and IR Ribavirin Combination We designed the clinical study described in Table 4 to determine the safety and pharmacokinetics of an extended release combination formulation of amantadine and oseltamivir co-administered with IR ribavirin.

EXAMPLE 11

A Phase 2 Clinical Trial of the Safety and Efficacy of intravenous Triple Combination Antiviral Drug Therapy for the Treatment of Severe Avian Influenza We designed this study to: 1) evaluate the safety and tolerability of i.v. triple combination antiviral drug therapy (TCAD) in the treatment of patients with severe avian influenza; 2) to evaluate the rate and extent of antiviral efficacy of TCAD over the course of treatment as assessed by negative transcriptase-polymerase chain reaction (RT-PCR) detection of viral ribonucleic acid (RNA) in upper and lower respiratory tract, gastrointestinal tract (feces), and blood (viremia), nose and throat; and 3) assess the rate and extent of antiviral drug resistance to TCAD over the course of treatment by pyrosequencing (or equivalent).

Study Size: 12 patients

Inclusion Criteria: 1) age $\geq 1$ year; 2) fever $\geq 38.0°$ C.; 3) at least one respiratory symptom: cough, dyspnea (shortness of breath), and/or sore throat; 4) illness (onset of fever, respiratory symptoms, or constitutional symptoms) begun in the last 7 days; and 5) have evidence of epidemiologic risk for avian influenza as defined by meeting, one of the following criteria within 14 days prior to the time of illness onset: (a) There were dead or sick birds within the subjects village or neighborhood (within a 2 km radius); (b) The subject had direct bird or poultry contact (either healthy or sick birds or poultry); (c) The subject had face-to-face contact with someone with known or suspected avian influenza; or (d) The subject had possible laboratory exposure to H5N1 virus.

Exclusion Criteria: 1) History of allergy or severe intolerance (as judged by the investigator) to amantadine hydrochloride, zanamivir, and/or ribavirin, and or to any components of these drug products; and 2) Alternate explanation for the patient's clinical symptoms (i.e. other than influenza) as determined by the investigator with the information immediately available.

TABLE 4

| | |
|---|---|
| Purpose | To determine the safety and pharmacokinetics of repeated doses of drug. |
| Dosage: | Dosing selected is based on previous single ascending dose (SAD) study: e.g. 100 mg amantadine SR + 75 mg oseltamivir + 400 mg ribavirin, 100 mg amantadine SR + 75 mg oseltamivir + 600 mg ribavirin, 200 mg amantadine SR + 75 mg oseltamivir + 400 mg ribavirin, 200 mg amantadine SR + 75 mg oseltamivir + 600 mg ribavirin, 200 mg amantadine SR + 150 mg oseltamivir + 600 mg ribavirin, or 200 mg amantadine SR + 150 mg oseltamivir + 800 mg ribavirin, QD for 7 days |
| Concurrent Controls | Amantadine IR or amantadine IR plus oseltamivir IR (both dosed as per manufacturers' labels) |
| Route: | Oral |
| Subject Population: | Males or females diagnosed with influenza |
| Structure: | 4 arm |
| Study Sites: | TBD |
| Blinding: | Patients blinded |
| Method of Subject Assignment: | Random with equal number of males and females in each group and equal age distributions within groups |
| Total Sample Size: | 24 Subjects 6 per dosing arm |
| Primary Efficacy Endpoint: | None |
| Adverse Events: | Monitored at least twice daily for behavioral, cardiovascular, and gastrointestinal effects reported for high doses of amantadine or oseltamivir (including dizziness, headache, confusion, constipation, hypertension, coughing, nausea, diarrhea, vomiting). |
| Blood Collection | By cannula through first day of study period then 2-4 times daily for rest of study |
| Analysis | Assays to measure amantadine, oseltamivir, ribavirin and potentially other physiological parameters, adverse events |

Screening Criteria: 1) The following samples will be tested by qualitative RT-PCR for H5, however the decision to initiate TCAD therapy is not dependent upon receipt of the results from these tests: nasal swab×2; oropharyngeal (throat) swab×2; nasopharygeal aspirate (NPA; as the NPA is an obtrusive test for some subjects, the NPA can be omitted or a nasal wash can be substituted for the NPA at the discretion of the investigator); bronchial alveolar lavage (BAL) or endotracheal tube aspirate; blood sample (for viremia, CBC, and serum chemistry); and urine pregnancy for females ≧12 years old.

TCAD dosing regimen: The duration of treatment will be a minimum of 5 days, but may be extended as determined by the physician based on the benefit/risk assessment for each individual patient. A kit for 5 days of treatment contains: 1) 10 vials containing ~4 ml of 100 mg/ml amantadine in water with or without buffer, 2) 10 vials containing 15 ml of 75 mg/ml ribavirin in water with or without buffer, and 3) 10 vials of ~7 ml of 10 mg/ml zanamivir in water with or without buffer or, as an alternative to zanamivir, 10 vials of lyophilized oseltamivir.

For treatment, 3.3 ml from an amantadine vial is drawn into a syringe and injected into a 500 ml infusion bag of 0.9% or 5% dextrose/0.45% saline producing a concentration of 0.66 mg/ml of amantadine; the infusion volume rate is set to 40 ml/min, which results in an infusion dose rate of 26 mg/hour (630 mg/day). 13.5 ml from a ribavirin vial is drawn into a syringe and injected into a 500 ml infusion bag of saline producing a concentration of 2.03 mg/ml of ribavirin; the infusion volume rate is set to 40 ml/min, which results in an infusion dose rate of 84.6 mg/hour (2030 mg/day). 6.5 ml zanamivir is drawn into a syringe and injected into a 500 ml infusion bag of saline producing a concentration of 0.13 mg/ml of zanamivir; the infusion volume rate is set to 40 ml/min, which results in a infusion dose rate of 5.3 mg/hour (127 mg/day). Alternatively to the zanamivir, 5 ml of water is drawn into a syringe and injected into a vial of lyophilized oseltamivir to reconstitute the sterile powder producing a concentration of 46 mg/ml oseltamivir phosphate; the infusion volume rate is set to 40 ml/min, which results in an infusion dose rate of 18.4 mg/hour (442 mg/day). At these infusion rates new bags of each antiviral agent need to be prepared every 12 hours.

Safety: Adverse events will be monitored. The NIH Division of AIDS Table for Grading the Severity of Adult and Pediatric Adverse Events (DAIDS AE grading table) will be used to assess the severity of an adverse event.

Clinical Evaluations: Clinical evaluations include: in-hospital mortality; rate and extent of clinical failure over the course of treatment [clinical failure is defined as death, severe tachypnea (respiratory rate ≧30 for ages ≧12 years, rate ≧40 for ages 6 to 12 years, rate ≧45 for ages 3 to 6 years, rate ≧50 for ages 1 to 3 years); severe dyspnea (unable to speak full sentences, or use of accessory respiratory muscles); arterial oxygen saturation <92% on room air by trans-cutaneous method; need for mechanical ventilation or ICU admission]; 28-day mortality for subjects; 180-day mortality for subjects; use of mechanical ventilation at any time for subjects; number of ICU admissions for subjects with avian influenza; development of acute respiratory distress syndrome (ARDS) at any time for subjects; duration of hospitalization for subjects; duration of symptoms as defined by time to absence of fever, no or minimal symptoms, no need for relief medication, and resumption of normal activity.

Virologic Endpoints: Virologic evaluations include: rate and extent of viral load and shedding over the course of treatment as assessed by negative RT-PCR for viral RNA in nose and throat swabs, blood, NAL and BAL samples; rate and extent of the emergence of amantadine or zanamivir antiviral drug resistance as determined by pyrosequencing; and genetic characterization of resistant variants.

What is claimed is:

1. A kit for treating a patient wherein said patient has an influenza virus infection, is suspected of being infected with influenza, has a symptom associated with an influenza virus infection, or is at risk of exposure to an influenza virus, said kit comprising:
   a) an M2 inhibitor selected from amantadine and rimantadine in an amount that is antivirally effective in the combination;
   b) ribavirin in an amount that is antivirally effective in the combination, and
   c) a neuraminidase inhibitor (NAi) in an amount that is antivirally effective in the combination,
   wherein the M2 inhibitor and ribavirin are provided in amounts that achieve drug concentrations that increase sensitivity of an influenza virus to the NAi by at least 2-fold over sensitivity of the virus to the NAi when used as a monotherapy, as measured in an in vitro dose response assay using influenza-infected MDCK cells.

2. The kit of claim 1, wherein the M2 inhibitor and ribavirin are co-formulated.

3. The kit of claim 1 wherein each daily dose of the M2 inhibitor is 200 to 250 mg/day, and each daily dose of the ribavirin is 400 to 2400 mg/day.

4. The kit of claim 3 wherein the M2 inhibitor is provided in an extended release oral dosage form that provides a Tmax of at least 8 hours.

5. The kit of claim 3 or 4, wherein the M2 inhibitor is amantadine.

6. The kit of claim 1, wherein the neuramidase inhibitor (NAi) is oseltamivir, oseltamivir carboxylate, zanamivir, or peramivir.

7. The kit of claim 6, wherein the neuramidase inhibitor (NAi) is oseltamivir or oseltamivir carboxylate.

* * * * *